(12) United States Patent
Portoghese et al.

(10) Patent No.: US 9,981,043 B2
(45) Date of Patent: May 29, 2018

(54) ANALGESIC CONJUGATES

(71) Applicants: REGENTS OF THE UNIVERSITY OF MINNESOTA, Minneapolis, MN (US); Philip Portoghese, Minneapolis, MN (US); Akgun Eyup, Minneapolis, MN (US)

(72) Inventors: Philip Portoghese, Minneapolis, MN (US); Akgun Eyup, Minneapolis, MN (US)

(73) Assignee: Regents of the University of Minnesota, Minneapolis, MN (US)

(*) Notice: Subject to any disclaimer, the term of this patent is extended or adjusted under 35 U.S.C. 154(b) by 70 days.

(21) Appl. No.: 14/766,715

(22) PCT Filed: Feb. 7, 2014

(86) PCT No.: PCT/US2014/015395
§ 371 (c)(1),
(2) Date: Aug. 7, 2015

(87) PCT Pub. No.: WO2014/124317
PCT Pub. Date: Aug. 14, 2014

(65) Prior Publication Data
US 2015/0374836 A1 Dec. 31, 2015

Related U.S. Application Data

(60) Provisional application No. 61/762,732, filed on Feb. 8, 2013.

(51) Int. Cl.
| | | |
|---|---|---|
| *A61K 47/48* | (2006.01) | |
| *A61K 31/4168* | (2006.01) | |
| *A61K 31/4418* | (2006.01) | |
| *A61K 31/445* | (2006.01) | |
| *A61K 31/485* | (2006.01) | |
| *A61K 31/53* | (2006.01) | |
| *A61K 31/44* | (2006.01) | |
| *A61K 31/4468* | (2006.01) | |

(52) U.S. Cl.
CPC ........ *A61K 47/481* (2013.01); *A61K 31/4168* (2013.01); *A61K 31/44* (2013.01); *A61K 31/445* (2013.01); *A61K 31/4418* (2013.01); *A61K 31/4468* (2013.01); *A61K 31/485* (2013.01); *A61K 31/53* (2013.01)

(58) Field of Classification Search
None
See application file for complete search history.

(56) References Cited

U.S. PATENT DOCUMENTS

2007/0208028 A1 9/2007 Conn et al.
2009/0233841 A1 9/2009 Portoghese et al.

FOREIGN PATENT DOCUMENTS

WO 2006073396 A1 7/2006
WO WO 2006/073396 A1 * 7/2006

OTHER PUBLICATIONS

Carey, FA. Organic Chemistry 6th Ed. McGraw Hill. 2006, chapter 1, p. 9.*
Gabra, BH. et al. mGluR5 antagonist that block calcium mobilization in vitro also reverse (S)-3,5-DHPG-induced hyperalgesia and morphine antinociceptive tolerance in vivo. Brain Research. 2008, vol. 1187, p. 58.*
Akgun, et al., "Inhibition of Inflammatory and Neuropathic Pain by Targeting a Mu Opioid Receptor/Chemokine Receptor5 Heteromer (MOR-CCR5)", J. Med. Chem. 58 (21), 8647-8657 (2015).
Akgun, et al., "Ligands that interact with putative MOR-mGluR5 heteromer in mice with inflammatory pain produce potent antinociception", PNAS vol. 110 (28), 11595-11599 (2013).
Fischer, et al., "Increased efficacy of μ-opioid agonist-induced antinociception by metabotropic glutamate receptor antagonists in C57BL/6 mice: comparison with (--)-6-phosphonomethyl-decahydroisoquinoline-3-carboxylic acid (LY235959)", Psychopharmacology 198, 271-278 (2008).
Gabra, et al., "mGluR5 antagonists that block calcium mobilization in vitro also reverse (S)-3,5-DHPG-induced hyperalgesia and morphine antinociceptive tolerance in vivo", Brain Research 1187, 58-66 (2008).
Gasparini, et al., "[(3)H]-M-MPEP, a potent, subtype-selective radioligand for the metabotropic glutamate receptor subtype 5", Bioorg Med Chem Lett 12 (3), 407-409 (2002).
Guo, et al., "The role of glutamate and its receptors in mesocorticolimbic dopaminergic regions in opioid addiction", Neurosci Biobehav Rev 33 (6), 864-873 (2009).
Lee, et al., "Pharmacological Profiles of Oligomerized μ-Opioid Receptors", Cells 2, 689-714 (2013).
Patel, et al., "Species differences in mGluR5 binding sites in mammalian central nervous system determined using in vitro binding with [18F]F-PEB", Nucl Med Biol 34 (8), 1009-1017 (2007).
Patent Cooperation Treaty, International Searching Authority, Search Report and Written Opinion for PCT/US2014/015395, 12 pages, dated Jun. 10, 2014.
Schroder, et al., "Allosteric modulation of metabotropic glutamate receptor 5 affects phosphorylation, internalization, and desensitization of the micro-opioid receptor", Neuropharmacology 56 (4), 768-778 (2009).
Smeester, et al., "Targeting putative mu opioid/metabotropic glutamate receptor-5 heteromers produces potent antinociception in a chronic murine bone cancer model", Eur J Pharmacol. 743, 48-52 (2014).
Zheng, et al., "Induced association of mu opioid (MOP) and type 2 cholecystokinin (CCK2) receptors by novel bivalent ligands", J Am Chem 52, 247-258 (2009).

(Continued)

*Primary Examiner* — Heidi Reese
*Assistant Examiner* — Ben S Michelson
(74) *Attorney, Agent, or Firm* — Viksnins Harris Padys Malen LLP

(57) ABSTRACT

The invention provides analgesic conjugates having a mu opioid receptor agonist linked to a mGluR$_5$ antagonist, and to methods for producing analgesia using such compounds.

9 Claims, 10 Drawing Sheets

(56) References Cited

OTHER PUBLICATIONS

Portoghese, et al., "Opioid Agonist and Antagonist Bivalent Ligands as Receptor Probes", Life Sciences, 31(12 & 13), 1283-1286 (1982).

\* cited by examiner

US 9,981,043 B2

ANALGESIC CONJUGATES

PRIORITY OF THE INVENTION

This application claims priority to U.S. Provisional Application No. 61/762,732, which was filed on 8 Feb. 2013. The entire contents of this provisional application are hereby incorporated herein by reference.

STATEMENT REGARDING FEDERALLY SPONSORED RESEARCH OR DEVELOPMENT

This invention was made with government support under grant DA030316 awarded by the National Institutes of Health. The United States government has certain rights in the invention.

BACKGROUND OF THE INVENTION

The excitatory neurotransmitter, glutamate, in the CNS is an important mediator of opioid nociception, dependence, and withdrawal (Guo Y, Wang, et al., *Neurosci. Biobehav. Rev.*, 2009, 33(6):864-873). Glutamate exerts its effect via two different classes of glutamate receptors, ionotropic and metabotropic. Among the metabotropic receptors (mGluR), the metabotropic glutamate-5 receptor subtype (mGluR5) is widely distributed in the CNS (Patel S, et al. *Nucl. Med. Biol.*, 2007, 34, 1009-1017), where it modulates synaptic transmission, neuronal excitability, and plasticity. The mGluR$_5$ is a class-C G protein-coupled receptor (GPCR) whose activation is mediated by binding of glutamate to its extracellular Venus flytrap domain. It is noteworthy that the selective mGluR$_5$ antagonist, MPEP, acts allosterically by binding to the 7TM domain of the receptor (Gasparini F, et al., *Bioorg. Med. Chem. Lett.*, 2002, 407-409).

The low effectiveness of morphine and related mu opioid analgesics for the chronic treatment of inflammatory pain is well known. This is due to opioid-induced release of proinflammatory cytokines, which leads to increased levels of glutamate that lower the pain threshold via the mGluR5 and NMDAR. In this regard, the use of opioids with metabotropic glutamate-5 receptor (mGluR$_5$) antagonist has been reported to increase the efficacy of morphine and prevent the establishment of side effects during chronic use. Given the colocalization of opioid receptors and mGluR$_5$ in glia and neurons, together with reports that indicate coexpressed opioid/mGluR$_5$ receptors in cultured cells associate as heteromers, there is the possibility this could occur in vivo as well (Schröder H, et al., *Neuropharmacology*, 2009, 56(4), 768-778).

Morphine and many other analgesics have lower efficacy in treating pain associated with certain conditions such as cancer, serious burns, and spinal injury. Accordingly, there is currently a need for analgesic agents for treatment of pain for which current analgesics are ineffective.

SUMMARY OF THE INVENTION

The invention provides analgesic conjugates that are particularly useful for treating inflammatory pain associated with conditions such as cancer, serious burns, and spinal injury.

The analgesic conjugates disclosed herein have a mu opioid agonist linked to a mGluR$_5$ antagonist. Representative conjugates of the invention were evaluated for antinociception using the tail-flick assay in mice pretreated with LPS and the von Frey assay or in mice with bone cancer. Compound 4c (22-atom spacer) was the most potent member of the series tested (i.t. ED$_{50}$<9 fmol/mouse) either with the tail flick assay or the CFA-treated von Frey method. The analgesic conjugates of the invention are useful for treating chronic, intractable pain. The analgesic conjugates of the invention are also useful as pharmacologic tools for the investigation of the heteromer in vivo and in vitro.

Accordingly, the present invention provides an analgesic conjugate of the invention, which is a conjugate comprising a mu opioid agonist linked to a mGluR$_5$ antagonist.

The invention also provides a pharmaceutical composition comprising a conjugate of the invention and a pharmaceutically acceptable carrier. In one embodiment the pharmaceutical composition is suitable for spinal (e.g. epidural or intrathecal) administration.

The invention also provides a method for treating pain in an animal (e.g. a human) comprising administering a conjugate of the invention to the animal.

The invention also provides a conjugate of the invention for use in medical therapy.

The invention also provides the use of a conjugate of the invention to prepare a medicament for producing analgesia in an animal (e.g. a human).

The invention also provides a conjugate of the invention for the prophylactic or therapeutic treatment of pain.

DETAILED DESCRIPTION OF THE INVENTION

Figure 1:
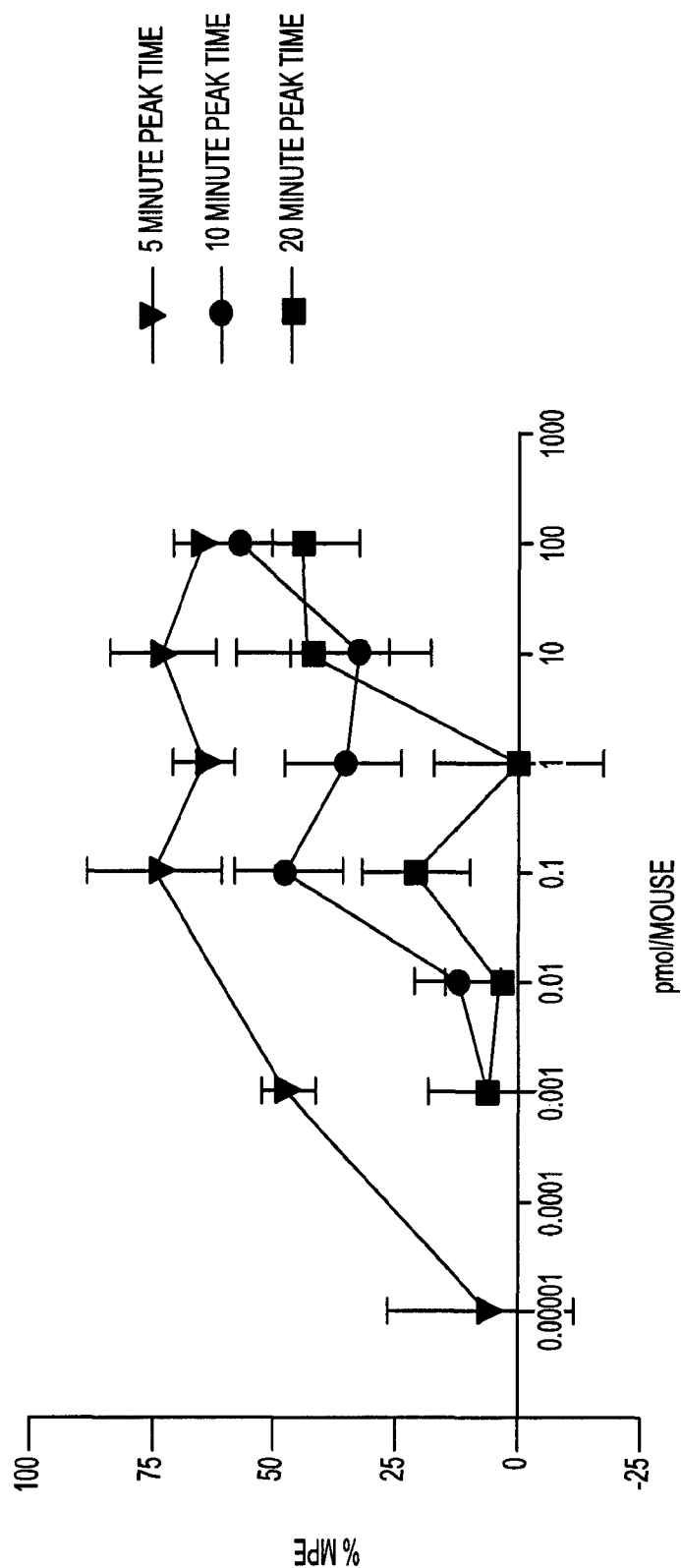
FIG. 1 Shows result of CFA studies using bivalent ligand 4c [ED$_{50}$: 7.66 fmol/mouse (0.22-260)] (Example 5).

A specific conjugate of the invention is a conjugate having the formula:

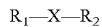

wherein
$R_1$ is a mu opioid receptor agonist;
$R_2$ is a mGluR$_5$ antagonist; and
X is a linker;
or a salt thereof.

Mu Opioid Receptor Agonists

A "mu opioid receptor agonist" refers to any compound that binds to a mu opioid receptor, e.g., selectively binds to a mu opioid receptor and activates the mu opioid receptor. The ability of a compound to act as a mu opioid receptor agonist may be determined using pharmacological methods well known in the art.

Mu opioid receptor agonists include, but are not limited to, oxymorphone, fentanyl, carfentanyl, α-oxymorphamine, benzomorphans, etonitazine,

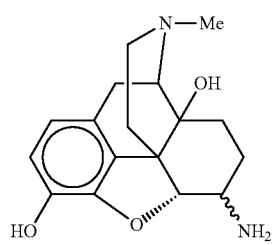

101

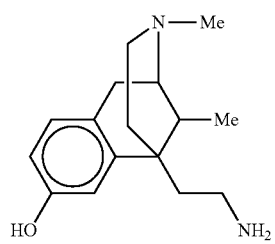

100

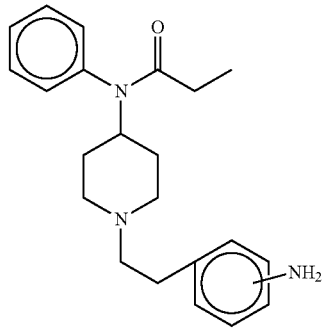

102

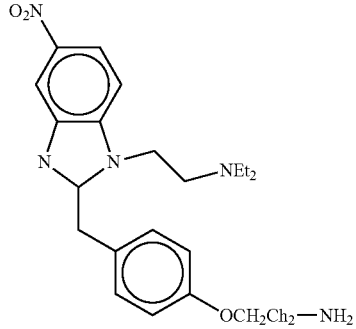

103

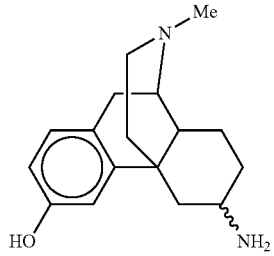

104 and derivatives thereof. The Mu opioid receptor agonists can be linked to the linker X through any synthetically feasible position on the Mu opioid receptor agonist. For example, the Mu opioid receptor agonist can be linked to the linker X through an ether, amine, ester, or amide linkage. A hydrogen or a functional group (e.g. a ketone) on the Mu opioid receptor agonist can also be converted to another functional group (e.g. a hydroxy group, oxime, or an amine) or removed to provide a residue of the Mu opioid receptor agonist with a suitable point of attachment for the linker X. Also, see Foye's Principles of Medicinal Chemistry, 5th Ed., D. A. Williams and T. L. Lemke, Eds, Lippencott, Williams, and Wilkins, and especially Chapter 19, including pages 462-465.

When the Mu opioid receptor agonist is oxymorphone it can be linked to the linker X through any synthetically feasible position on the oxymorphone. For example, it can be linked through an ether linkage or through an amide linkage as found in compound 4c. A suitable Mu opioid receptor agonist that can be incorporated into a conjugate of the invention is a compound of the following formula:

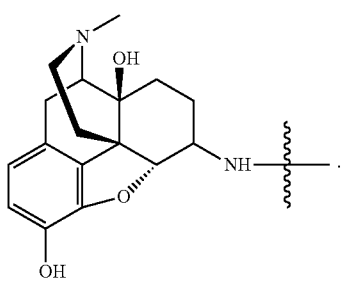

Another suitable Mu opioid receptor agonist that can be incorporated into a conjugate of the invention is a compound of the following formula:

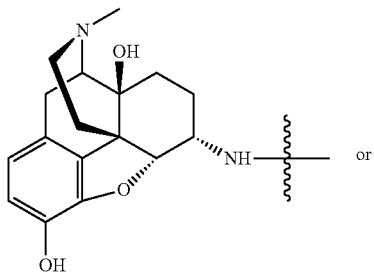

or

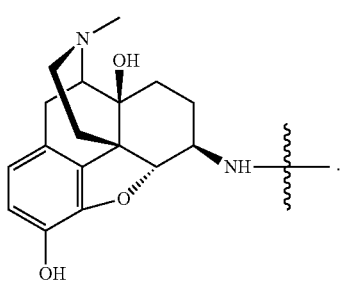

When the Mu opioid receptor agonist is fentanyl it can be linked to the linker X through any synthetically feasible position on the fentanyl molecule. For example, it can be linked through an amine linkage or through an amide linkage. A suitable Mu opioid receptor agonist that can be incorporated into a conjugate of the invention is a compound of the following formula:

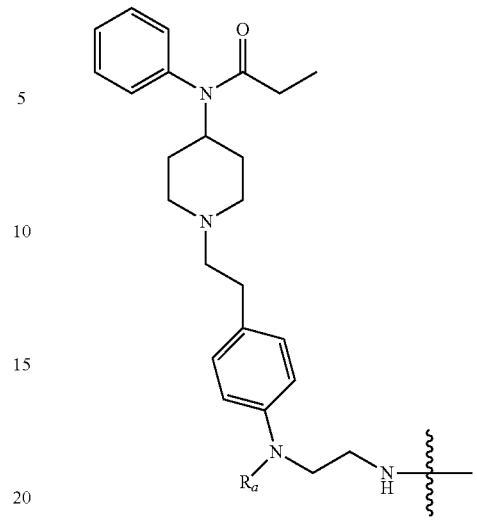

wherein $R_a$ is H or methyl.

When the Mu opioid receptor agonist is carfentanyl it can be linked to the linker X through any synthetically feasible position on the carfentanyl molecule. For example, it can be linked through an amine linkage or through an amide linkage. A suitable Mu opioid receptor agonist that can be incorporated into a conjugate of the invention is a compound of the following formula:

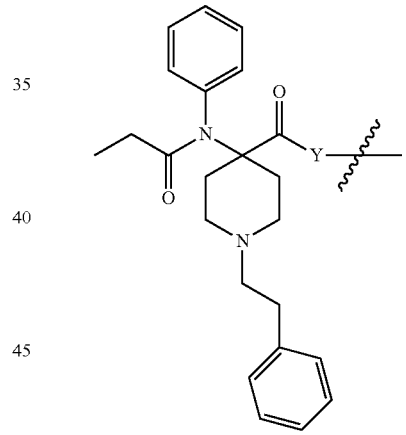

wherein Y is O or —$NR_b$—; wherein $R_b$ is H or methyl.

mGluR$_5$ Antagonist

A "mGluR$_5$ antagonist" refers to any compound that attenuates the effects of a mGluR$_5$ receptor agonist. The ability of a compound to act as a mGluR$_5$ antagonist may be determined using pharmacological methods well known in the art. The mGluR$_5$ antagonist can be linked to the linker X through any synthetically feasible position on the mGluR$_5$ antagonist. For example, the mGluR$_5$ antagonist can be linked to the linker X through an ether, amine, ester, or amide linkage. A hydrogen or a functional group (e.g. a ketone) on the mGluR$_5$ antagonist can also be converted to another functional group (e.g. a hydroxy group, oxime, or an amine) or removed to provide a residue of the mGluR$_5$ antagonist with a suitable point of attachment for the linker X.

mGluR$_5$ Antagonist include, but are not limited to the following compounds:

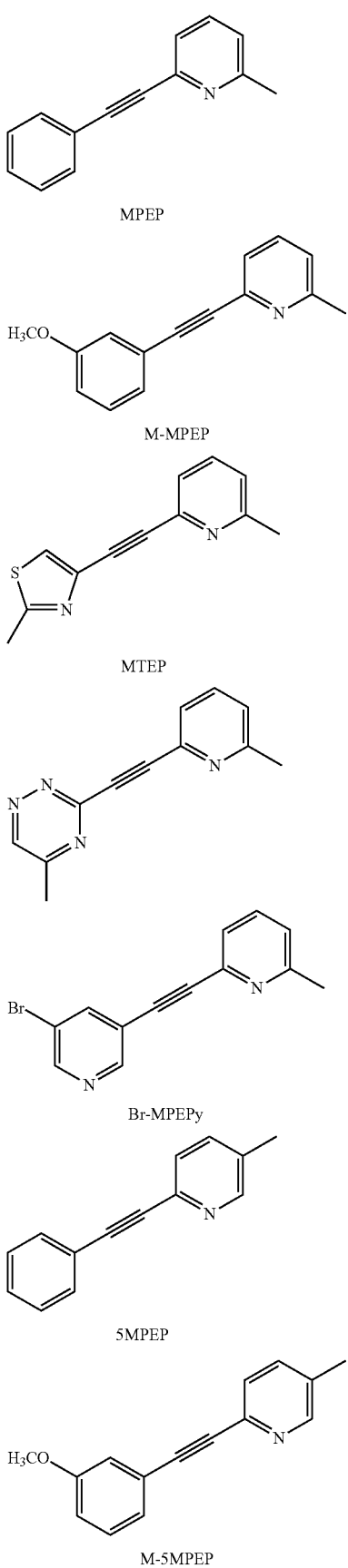

MPEP

M-MPEP

MTEP

Br-MPEPy

5MPEP

M-5MPEP

-continued

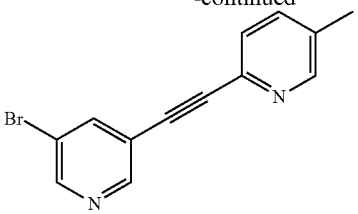

Br-5MPEPy

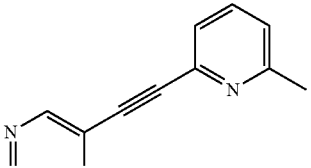

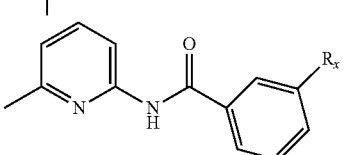

$R_x$ = CN, Cl, Ph

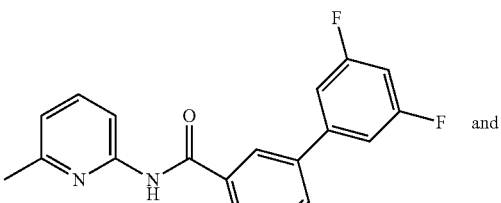 and

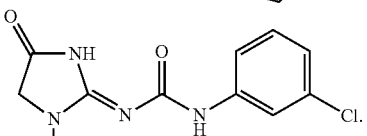

Fenobam

In one embodiment the mGluR$_5$ antagonist is 2-methyl-6-((3-methoxyphenyl)ethynyl)-pyridine (i.e. m-methoxy-MPEP).

A suitable mGluR$_5$ antagonist that can be incorporated into a conjugate of the invention is a compound of the following formula:

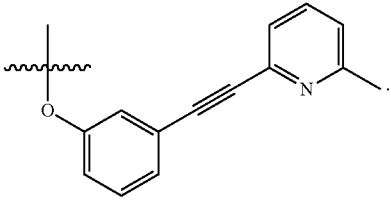 [SMILES: *Oc1cccc(C#Cc2cccc(C)n2)c1]

Linker

The conjugates of the invention have a mu opioid receptor agonist linked via a linker to a mGluR$_5$ antagonist. The attachment of the linker to the pharmacophores, e.g., the point of attachment, should not eliminate the pharmacophores' activity as a mu opioid receptor agonist or as a mGluR$_5$ antagonist. The linker length may be varied in certain embodiments of the invention by increasing or decreasing the number of atoms in the linker (e.g., by varying the number of methylenes in the central diamine portion. In some embodiments of the invention, the linkers vary from 16 atoms to 21 atoms.

In some embodiments of the invention, the linker length is about 16, 17, 18, 19, 20, 21, 22, 23, 24, or 25 Å long. In some embodiments of the invention, the linker length is from about 22 to 26 Å. In some embodiments of the invention, the linker length is 16, 17, 18, 19, 20, 21, 22, 23, 24, or 25 atoms long. In some embodiments, the linker is 18-24 atoms long. The art worker can calculate the length of a specific linker using molecular modeling software available to the art worker, for example, using Chem3D Pro 9.0 (CambridgeSoft Corporation).

Linkers may contain amino acids, peptides, and glycolic acids.

The term "amino acid," includes the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also includes natural and unnatural amino acids bearing a conventional amino protecting group (e.g. acetyl or benzyloxycarbonyl), as well as natural and unnatural amino acids protected at the carboxy terminus (e.g. as a $(C_1-C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "peptide" describes a sequence of 2 to 35 amino acids or peptidyl residues. The sequence may be linear or cyclic. For example, a cyclic peptide can be prepared or may result from the formation of disulfide bridges between two cysteine residues in a sequence. Peptide derivatives can be prepared, for example, as disclosed in U.S. Pat. Nos. 4,612,302; 4,853,371; and 4,684,620.

The linker is in some embodiments a divalent organic radical having a molecular weight of from about 25 daltons to about 400 daltons. The linker in some embodiments has a molecular weight of from about 40 daltons to about 200 daltons.

The linker may be biologically inactive, or may itself possess biological activity. The linker can also include other functional groups (including hydroxy groups, mercapto groups, amine groups, carboxylic acids, as well as others) that can be used to modify the properties of the conjugate (e.g. for branching, for cross linking, for appending other molecules (e.g. a biologically active compound) to the conjugate, for changing the solubility of the conjugate, or for effecting the biodistribution of the conjugate).

In some embodiments of the invention, $X_1$ includes an amino acid. In some embodiments of the invention, $X_1$ includes a peptide.

In some embodiments of the invention, the linker X is a divalent, branched or unbranched, saturated or unsaturated, hydrocarbon chain, having from 10-30 carbon atoms in the chain, wherein one or more of the carbon atoms in the chain is optionally replaced by (—O—) or (—NH—).

In some embodiments of the invention, the linker X is a divalent, branched or unbranched, saturated or unsaturated, hydrocarbon chain, having from 10-30 carbon atoms in the chain, wherein one or more of the carbon atoms in the chain is optionally replaced by (—O—) or (—NH—), and wherein the chain is optionally substituted on at least one carbon, —O— or —NH— with one or more substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

In some embodiments of the invention, the linker X is a chain 18-24 atoms in length.

It should be understood that any linker that provides an active conjugate of the invention can be used. Certain linkers may confer or maintain a favorable hydrophilic-lipophilic balance for access into the central nervous system (CNS) upon administration to a location outside of the CNS, e.g., via oral or parenteral administration. For example, the linker may have hydrophobic and hydrophilic groups in repeating units so that lengthening the linker would not substantively alter the balance of the conjugate.

Several linkers are presented herein, and there are numerous other possible linkers that could also be used. The linkers can be homologated to afford the conjugate with a particular combination of pharmacophores. Regioisomers and stereoisomers of the pharmacophores also may be used, e.g., due to the NH substitution on the pharmacophores.

A specific linker is a linker of greater than about 16 atoms. In certain embodiments of the invention the length of the linker X may be selected so that it bridges the recognition sites of the mu and mGluR₅ receptors.

In some embodiments, the linker is a divalent, branched or unbranched, saturated or unsaturated, hydrocarbon chain, having from 1 to 50, e.g, from 10 to 30, e.g., from 20 to 30, carbon atoms, wherein the chain is optionally substituted on at least one carbon atom with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy. One or more of the carbon atoms may be optionally replaced by another atom such as (—O—) or (—N—). The chain may also be optionally substituted on at least one carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

In some embodiments of the invention, the linker may be:
CO—CH₂OCH₂CO—NH—(CH₂)$_{n2}$NH—CO—CH₂OCH₂CO;
CO—CH₂O(CH₂CH₂O)$_{n3}$CH₂CO;
(CO—CH₂NH)$_{x2}$—CO—(CH₂)$_{n4}$—CO—(NH—CH₂CO)$_{x2}$;
CO—(CH₂)$_{n3}$CO; or

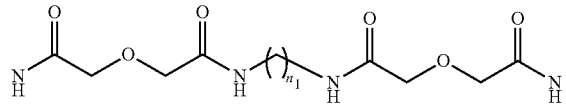

300 wherein $n_1$ is any integer from 1-10, $n_2$ is any integer from 1-8, $n_3$ is any integer from 1-20, $n_4$ is any integer from 12-22, and x2 is any integer from 1-2.

Specific values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

It will be appreciated by those skilled in the art that conjugates of the invention having a chiral center may exist in and be isolated in optically active and racemic forms. Some conjugates may exhibit polymorphism. It is to be understood that the present invention encompasses any racemic, optically-active, polymorphic, or stereoisomeric form, or mixtures thereof, of a conjugate of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a conjugate formula herein is drawn in a non-stereochemical manner (e.g. flat), the atom to which the bond is attached includes all stereochemical possibilities. When a bond in a conjugate formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the conjugate may be at least 51% the absolute stereoisomer depicted. In another embodiment, the conjugate may be at least 60% the absolute stereoisomer depicted. In another embodiment, the conjugate may be at least 80% the absolute stereoisomer depicted. In another embodiment, the conjugate may be at least 90% the absolute stereoisomer depicted. In another embodiment, the conjugate may be at least 95 the absolute stereoisomer depicted. In another embodiment, the conjugate may be at least 99% the absolute stereoisomer depicted.

Analgesia

Analgesia refers to a state in which a painful stimulus elicits a decreased sensation of pain as compared to the pain sensation elicited without analgesia. Analgesic effectiveness of drugs in humans is predicted by the tail flick test, and can be evaluated using methods known to the art worker, e.g., using the radiant heat tail flick assay. Briefly, in the radiant heat tail flick assay, a beam of light is focused on a mouse tail and the time until the tail flicks is measured. Each animal may serve as its own control and may be used only once. Mice are tested once before injection of a drug (control time). After injection of the drug, the mice are tested at the time of peak drug response (drug time). The light intensity can be adjusted so that control times are between 1.5 and 2.5 seconds. A 10 second cutoff drug time can be set to minimize the risk of tissue damage. Percent maximum possible effect (% MPE) is calculated as follows (Harris L S & Pierson A K, J. Pharmacol. Exp. Ther., 1964, 143(2):141-148,):

$$\frac{\text{Drug Time (s)} - \text{Control Time (s)}}{10 \text{ seconds} - \text{Control Time (s)}} \times 100\% = \% \text{ } MPE$$

Graded dose response curves of at least 3 doses with at least 8 mice per dose can be generated from the % MPE data. $ED_{50}$ values with 95% confidence intervals can be computed with GraphPad Prism using nonlinear regression methods.

In certain embodiments of the invention, the conjugates are used to cause analgesia to treat pain, e.g., acute and/or chronic pain. In some embodiments of the invention, the conjugates cause their analgesic effects in the central nervous system. Thus, the ability of the conjugates to pass through the blood brain barrier to allow for IV administration is advantageous.

Addiction, Dependence, and Tolerance

Addiction refers to the development of dependence, e.g., physical dependence, on a drug. Development of tolerance to a drug may occur so that when a drug has been administered for a period of time, the same dosage of that drug produces less of an effect, thereby leading to the need for increasing the dosage of that drug to achieve the same effect, e.g., the same amount of analgesia. Physical dependence on a drug may also occur when a drug has been administered for a period of time and the drug administration is terminated, leading to symptoms of drug withdrawal. Addiction to a drug can occur after chronic drug administration. Addiction liability refers to the potential of a drug to be abused for its rewarding properties, e.g., to the presumed preference of a subject to a specific drug so that a subject will prefer to remain in an environment associated with use of that drug.

To investigate the addiction, physical dependence, and tolerance associated with a compound, chronic ICV administration studies can be performed in mice. The compound of interest can be administered ICV via a cannula using an osmotic minipump for a period of time, e.g., for 3 days. Withdrawal can be measured by administering naloxone (1 mg/kg; subcutaneous (sc)) and counting the naloxone-precipitated jumps for 10 minutes. Tolerance can be determined by administering challenge dosed of the compound after chronic infusion for 3 days, and determining the chronic $ED_{50}$ value at that time.

The conditioned place preference (CPP) test is a technique used to measure the rewarding properties and addiction liability of a drug. Briefly, two sides of a CPP apparatus may have both visual and tactile differences, so that an animal can distinguish between the sides. On the first day of testing, the time each animal spends in either side of the apparatus is measured. For the next three days, a drug is "paired" with one side or the other by injecting the animal and immediately confining it to that side. On the final day, the amount of time the animal spends in the drug-paired side is determined and the percent change is calculated. If the percent change is positive, the drug is rewarding and presumed to be addictive.

Constipation

Constipation can be caused by inhibition, e.g., opioid-induced inhibition, of gastrointestinal (GI) transit. To evaluate the effect a drug has on GI transit, the drug can administered IV via the tail vein, e.g., in a volume of 100 µl to mice. Fifteen minutes later, charcoal meal (300 µl, oral) can be administered by gavage. Thirty minutes after the charcoal meal, the mice can be sacrificed by halothane overdose and the distance the charcoal traveled relative to the entire length of the GI tract can be compared to the distance traveled in control animals injected with saline. A drug that inhibits GI transit will decrease the distance the charcoal travels and will cause constipation.

Potency

The analgesic potency of a compound can be determined by methods known to the art worker, e.g., the potency may be determined by the tail flick assay and by mechanical hypersensitivity.

In some embodiments of the invention, the conjugates are at least about as potent as morphine; are at least about 10 times as potent as morphine, at least about 50 times as potent as morphine, or at least about 100 times as potent as morphine.

In cases where conjugates are sufficiently basic or acidic to form stable nontoxic acid or base salts, administration of the conjugates as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The conjugates can be formulated as pharmaceutical compositions and administered to a mammalian host, such as a human patient, in a variety of forms adapted to the chosen route of administration, i.e., orally or parenterally, by intravenous, intramuscular, topical or subcutaneous routes.

Thus, the conjugates may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the conjugate may be combined with one or more excipients and used in the form of ingestible tablets, buccal tablets, troches, capsules, elixirs, suspensions, syrups, wafers, and the like. Such compositions and preparations may contain at least 0.1% of active compound. The percentage of the compositions and preparations may, of course, be varied and may conveniently be between about 2 to about 60% of the weight of a given unit dosage form. The amount of conjugate in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The conjugate may also be administered intravenously, intraarterially, or intraperitoneally by infusion or injection. Solutions of the conjugate or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders including the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium including, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin. In some embodiments of the invention, the pharmaceutical dosage contains a pharmaceutically-acceptable carrier other than saline, and in some embodiments does not contain saline. In some embodiments of the invention, the pharmaceutical dosage contains saline and at least one other pharmaceutically-acceptable carrier.

Sterile injectable solutions are prepared by incorporating the conjugate in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

In one embodiment of the invention the conjugate of the invention is formulated for administration via a spinal route of administration. As used herein a spinal route of administration includes epidural and intrathecal administration.

For topical administration, the present conjugates may be applied in pure form. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the conjugates can be determined by comparing their in vitro activity, and in vivo activity in animal models. Methods for the extrapolation of effective dosages in mice, and other animals, to humans are known to the art; for example, see U.S. Pat. No. 4,938,949.

In some embodiments, the concentration of the conjugate in a liquid composition, such as a lotion, will be from about 0.1-25 wt-%, preferably from about 0.5-10 wt-%. The concentration in a semi-solid or solid composition such as a gel or a powder can be about 0.1-5 wt-%, preferably about 0.5-2.5 wt-%.

The amount of the conjugate, or an active salt or derivative thereof, required for use in treatment will vary not only with the particular conjugate selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

One or more of the conjugates can be administered by any route appropriate for the condition being treated. Suitable routes include transdermal, oral, rectal, nasal, topical, buccal, sublingual, vaginal, parenteral, subcutaneous, intramuscular, intravenous, intraarterial, intradermal, intrathecal, epidural, and the like.

Methods of Making the Compounds of the Invention

The invention also relates to methods of making the conjugates and compositions of the invention. The compositions are prepared by any of the applicable techniques of organic synthesis. Many such techniques are well known in the art. However, many of the known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., *Advanced Organic Chemistry*, Third Edition, (John Wiley & Sons, New York, 1985), *Comprehensive Organic Synthesis. Selectivity, Strategy & Efficiency in Modern Organic Chemistry. In 9 Volumes*, Barry M. Trost, Editor-in-Chief (Pergamon Press, New York, 1993 printing).

A number of methods for the preparation of the conjugates and compositions of the invention are provided herein. These methods are intended to illustrate the nature of such preparations are not intended to limit the scope of applicable methods.

The invention will now be illustrated by the following non-limiting Examples.

Example 1: Chemical Synthesis

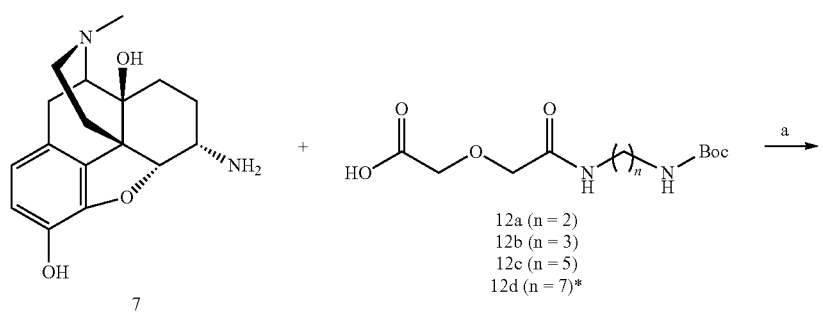

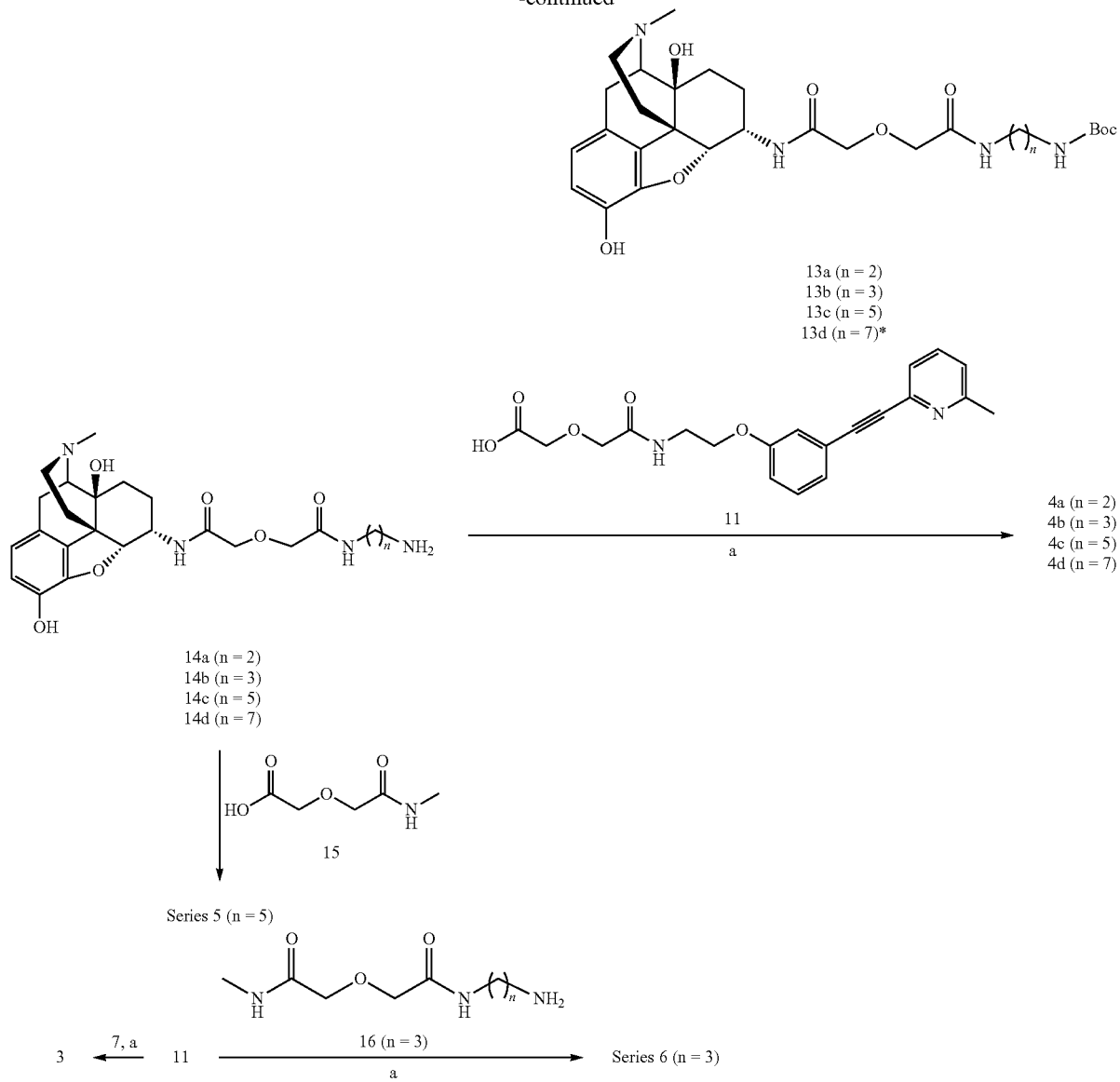

a HOBt/DCC, DMF, 50° C.; )* Cbz protected amine was used!

Synthetic scheme for bivalent ligands 3, 4a-4d, and monovalent ligands 5-6.

General.

Oxymorphone was obtained from Mallinckrodt & Co. All other chemicals and solvents were purchased from Aldrich or Fisher without further purification. $^1$H and $^{13}$C NMR spectroscopy were obtained on 300 MHz on an Oxford Varian VXR 300 MHz NMR Spectrometer. Mass spectroscopy was obtained on Bruker BioTOF II mass spectrometry. Purities of bivalent ligands (3), (4a-d), and the monovalent ligands (5-6) were over 98% based on analysis on HPLC column (Phenomenex Luna SB-C18 (2) 5u 4.6×250 mm) which was eluted with MeOH/Buffer (60:40) at a flow rate of 1 ml/min.

2-((3-methoxyphenyl)ethynyl)-6-methylpyridine, M-MPEP (2)

To a solution of hydroxy-MPEP (2a) in Hünig base in MeOH:MeCN (1:9, 5 mL) was added TMS diazomethane (38) (2M solution in Et$_2$O) dropwise. The reaction was allowed to stir for 1 hr. Removal of solvents in vacuum provided crude product. $^1$HNMR analysis indicated the formation of desired product 2(3).

N-((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)-2-(2-((2-(3-((6-methylpyridin-2-yl)ethynyl)phenoxy)ethyl)amino)-2-oxoethoxy)acetamide (3)

To acid 11 (0.146 g, 0.396 mmol) was added HOBt (0.059 g, 0.436 mmol), DCC (0.99 g, 0.476 mmol) and DMF (4 ml, 0.1M) followed by addition of α-oxymorphamine (7) (0.120 g, 0.396 mmol). After 24 h. TLC analysis indicated completion of reaction. The reaction mixture was filtered to remove urea followed by DMF removal in vacuum to crude product which was further purified on SiO$_2$ column chromatography using EtOAc (100%), and then the mixture (CH$_2$Cl$_2$/MeOH/NH$_4$OH, 95/4/1, v/v/v) as solvent to give 0.185 g (76%) of 3 as light yellow semi-solid. $^1$H NMR (400 MHz, CD$_3$OD) 7.72 (t, 7.6 Hz, 1H), 7.39 (d, 8 Hz, 1H), 7.26-7.31 (m, 2H), 7.14-7.16 (m, 2H), 6.98-7.01 (m, 1H), 6.64 (d, 8.4 Hz, 1H), 6.52 (d, 8.4 Hz, 1H), 4.48-4.53 (m, 2H), 4.07-4.14 (m, 6H (one m and two singlet's), 3.62-3.73 (m, 2H), 3.12 (br d, 18.4 Hz, 1H), 2.79 (d, 6.4 Hz, 1H), 2.53-2.80 (m, 1H), 2.52 (s, 3H), 2.42 (d, 7.2 Hz, 1H), 2.53 (s, 3H), 2.25 (d, 8.0 Hz, 2H), 1.64-1.72 (m, 1H), 1.37-1.55 (m, 3H), 0.97-1.08 (m, 1H). $^{13}$C NMR (100 MHz) 171.93, 170.74, 159.99, 159.91, 146.98, 143.01, 139.34, 138.65, 131.87, 130.83, 126.62, 125.76, 125.58, 124.41, 124.22, 120.28, 118.48, 118.47, 117.14, 90.30, 90.20, 89.00, 71.55, 71.16, 67.46, 65.78, 47.55, 47.15, 45.83, 43.37, 39.63, 34.46, 30.31, 23.90, 22.99, 21.58. MS (ESI)-TOF observed 653.3360 (M+1)$^+$, 675.3173 (M+Na$^+$), required exact mass 652.2897.

N-((4aS,7S,7aR,12bS)-4a,9-dihydroxy-3-methyl-2,3, 4,4a,5,6,7,7a-octahydro-1H-4,12-methanobenzofuro [3,2-e]isoquinolin-7-yl)-2-((14-(3-((6-methylpyridin-2-yl)ethynyl)phenoxy)-2,7,11-trioxo-9-oxa-3,6,12-triazatetradecyl)oxy)acetamide (4a))

To the mixture of acid 11 (freshly prepared!, 0.142 g, 0.385 mmol, 1.1 eq), HOBt (0.069 g, 0.510 mmol, 2.0 eq), DCC (0.105 g, 0.510 mmol, 2.0 eq) at 0° C. was added DMF (2 mL) and stirred for 15 min. A light yellow precipitated solution resulted. To this solution of amine 14a (0.162.5 g, 0.351 mmol, 1.0 eq) in a solvent mixture of Hünig base/DMF (3 mL, 1/5, v/v) was added. The ice-water bath was removed and the reaction was allowed to stir at rt for 17 h. MS (ESI) of crude reaction mixture indicated the formation of the desired product. The solvent was removed in vacuum and further purification was performed over silica gel column chromatography using the mixture (CH$_2$Cl$_2$/MeOH/NH$_4$OH, 97/2.5/0.5, 95/4/1 to 89/10/1, v/v/v). The final product 4a was isolated as amorphous light yellow solid (0.170 g, 60% yield). $^1$H NMR (400 MHz, CDCl$_3$) δ 7.21 (t, 8 Hz, 2H), 7.14 (d, 8.0 Hz, 1H), 7.10-7.04 (m, 3H), 7.03 (t, 8.0 Hz, 2H), 7.02 (br s, 1H), 6.98-7.01 (m, 1H), 6.90 (d, d, 8 Hz, 3.6 Hz, 1H), 6.73 (d, 8 Hz, 1H), 6.52 (d, 8 Hz, 1H), 450-4.55 (m, 2H), 4.05-4.09 (m, 8H), 4.01 (d, 4 Hz, 1H), 3.69-3.72 (m, 2H), 3.38-3.41 (p, 6.4 Hz, 2H), 3.27-0.99 (unidentified peaks). $^{13}$C NMR (100 MHz) δ 170.62, 169.99, 169.25, 168.09, 158.85, 158.23, 145.51, 142.19, 138.08, 136.71, 130.78, 129.57, 125.35, 124.86, 124.55, 123.25, 122.92, 119.33, 117.51, 115.92, 89.21, 88.73, 88.57, 76.86, 70.88, 70.71, 70.58, 70.36, 69.60, 66.33, 64.51, 53.50, 46.37, 45.83, 44.74, 43.05, 40.07, 39.07, 38.62, 33.31, 29.63, 29.11, 25.07, 24.35, 22.54, 22.07, 21.05. MS (ESI)-TOF observed 811.3301 (M+1)$^+$, required for C$_{43}$H$_{50}$N$_6$O$_{10}$ 810.3588.

N-((4aS,7S,7aR,12bS)-4a,9-dihydroxy-3-methyl-2,3, 4,4a,5,6,7,7a-octahydro-1H-4,12-methanobenzofuro [3,2-e]isoquinolin-7-yl)-2-((1-(3-((6-methylpyridin-2-yl)ethynyl)phenoxy)-4,8,14-trioxo-6-oxa-3,9,13-triazapentadecan-15-yl)oxy)acetamide (4b)

To the mixture of acid 11 (freshly prepared!, 0.118 g, 0.321 mmol, 1.3 eq), HOBt (0.067 g, 0.593 mmol, 2.0 eq), and DCC (0.102 g, 0.593 mmol, 2.0 eq) at 0° C., DMF (2 mL) was added and stirred for 15 min. A light yellow precipitated solution resulted. To this solution, a solution of amine 14b (0.126 g, 0.246 mmol, 1.0 eq) dissolved in the mixture of Hünig base/DMF (3 mL, 1/5, v/v) was added. The ice-water bath was removed and the reaction was allowed to stir at rt for 17 h. MS (ESI) of crude reaction mixture indicated the formation of the desired product. Then, the solvent was removed in vacuum and further purification was performed over silica gel column chromatography using the solvent mixture (CH$_2$Cl$_2$/MeOH/NH$_4$OH, 97/2.5/0.5, 95/4/1 to 89/10/1, v/v/v). The final product 4b was isolated as amorphous light yellow solid (0.067 g, 33% yield). $^1$H NMR (400 MHz, CDCl$_3$) δ 7.94 (t, 5.6 Hz, 1H), 7.82-7.88 (m, 2H), 7.61 (t, 7.6 Hz, 1H), 7.36 (d, 7.6 Hz, 1H), 7.20-7.28 (m, 2H), 7.13 (d, d, 8 Hz, 4 Hz, 2H), 7.03 (br s, 1H), 6.86 (dd, 8 Hz, 2 Hz, 1H), 6.70 (d, 8 Hz, 1H), 6.51 (d, 8.0 HZ, 1H), 4.51-4.58 (m, 2H), 4.00-4.08 (m, 8H), 3.64-3.67 (m, 2H), 3.30-3.42 (m, 4H), 3.08 (d, 19.2 Hz, 1H), 2.78 (d, 6.4 Hz, 1H), 2.50-2.58 (m, 4H), 2.34 (s, 3H), 2.15-2.41 (m, 6H), 1.69-1.70 (m, 3H), 1.49-1.56 (m, 2H), 1.33-1.39 (m, 1H), 1.25 (m, 1H), 0.98 (m, 1H). $^{13}$C NMR (100 MHz) δ 169.97, 168.94, 168.91, 167.95, 158.71, 158.14, 145.14, 142.01, 137.95, 136.79, 130.71, 129.50, 125.29, 124.63, 124.50, 123.09, 122.94, 119.21, 117.55, 115.41, 70.97, 70.74, 70.45, 70.40, 69.51, 66.32, 64.45, 46.27, 45.63, 44.71, 42.95, 38.36, 35.55, 34.89, 33.14, 29.54, 28.99, 28.95, 28.87, 24.15, 21.98, 20.99. MS (ESI)-TOF observed 825.1723 (M+1), 847.1372 (M+Na$^+$), required for C$_{44}$H$_{52}$N$_6$O$_{10}$ 824.3745.

N-((4aS,7S,7aR,12bS)-4a,9-dihydroxy-3-methyl-2,3, 4,4a,5,6,7,7a-octahydro-1H-4,12-methanobenzofuro [3,2-e]isoquinolin-7-yl)-2-((1-(3-((6-methylpyridin-2-yl)ethynyl)phenoxy)-4,8,16-trioxo-6-oxa-3,9,15-triazaheptadecan-17-yl)oxy)acetamide (4c)

To the mixture of acid 11 (freshly prepared!, 0.142 g, 0.385 mmol, 1.11 eq), HBTU (0.265 g, 0.695 mmol, 2.0 eq) and HOBt solution (1.40 mL of 0.5M HOBt solution in DMF, 0.695 mmol, 2.0 eq) was added at room temperature and stirred for 0.5 h. A light yellow solution with no precipitate resulted. To this solution, a solution of amine 14c (0.200 g, 0.348 mmol, 1.0 eq) dissolved in the solvent mixture of Hünig base/DMF (3 mL, 1/5, v/v) was added. The reaction was allowed to stir at rt for 20 h. Then, the solvent was removed in vacuum and further purification was performed over silica gel column chromatography using the solvent mixture (CH$_2$Cl$_2$/MeOH/NH$_4$OH, 95/4/1 to 92/7.5/0.5, v/v/v). The final product 4c was isolated as amorphous off white solid (0.251 g, 85% yield). $^1$H NMR (400 MHz, CDCl$_3$) δ 7.62 (t, 8 Hz, 2H), 7.36 (d, 8.0 Hz, 1H), 7.22-7.27 (m, 3H), 7.15 (t, 8.0 Hz, 2H), 7.06 (br s, 1H), 6.98-7.01 (m, 1H), 6.90 (dd, 8 Hz, 3.6 Hz, 1H), 6.73 (d, 8 Hz, 1H), 6.52 (d, 8 Hz, 1H), 450-4.55 (m, 2H), 4.05-4.09 (m, 8H), 4.01 (d, 4 Hz, 1H), 3.69-3.72 (m, 2H), 3.38-3.41 (p, 6.4 Hz, 2H), 3.27-3.32 (m, 4H), 3.10 (d, 19 Hz, 1H), 2.85 (dd, 13.2 Hz, 7.2 Hz, 2H), 2.76 (d, 6.4 Hz, 1H), 2.57 (s, 3H), 2.16-2.41 (m, 3H), 2.33 (s, 3H), 1.70-1.80 (m, 1H), 1.50-1.62 (m, 6H), 1.29-1.36 (m, 3H), 0.99-1.20 (m, 1H). $^{13}$C NMR (100 MHz) δ 169.36, 169.22, 169.01, 168.49, 158.63, 158.03, 145.59, 142.04, 138.05, 136.52, 130.50, 129.39, 125.15, 124.63, 124.36, 123.04, 122.71, 119.12, 117.73, 117.23, 115.72, 89.16, 88.48, 88.39, 71.15, 70.98, 70.67, 69.42, 66.11, 64.35, 51.88, 46.16, 45.62, 44.53, 42.88, 41.02, 38.90, 38.38, 38.26, 33.15, 29.04, 28.49, 28.24, 24.18, 23.46, 21.83, 20.96, 14.20. MS (ESI)-TOF observed 853.3502 (M+1), 875.3254 (M+Na$^+$), required for $C_{46}H_{56}N_6O_{10}$ 852.4058.

N-((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)-2-((1-(3-((6-methylpyridin-2-yl)ethynyl)phenoxy)-4,8,18-trioxo-6-oxa-3,9,17-triazanonadecan-19-yl)oxy)acetamide (4d)

A solution of carboxylic acid 11 (158 mg, 0.42 mmol, 1 eq), DCC (97.3 mg, 0.47 mmol, 1.1 eq), and HOBt (64 mg, 0.47 mmol, 1.1 eq) in DMF (4 mL) was stirred at rt. for 20 min. To this mixture, the amine 14d (217 mg, 0.40 mmol, about 1 eq) was added in one portion, and the reaction mixture was stirred under $N_2$ at 50° C. for 24 h. The DCU precipitate was collected via vacuum filtration and the filtrate was added to ethyl ether (100 mL) to facilitate precipitation of the crude product. The crude product was isolated by vacuum filtration and purified further via flash chromatography (silica gel, $CH_2Cl_2$/MeOH/NH$_4$OH, 85/14.5/0.5, v/v/v). Yield: 40 mg, 11%. $^1$H-NMR (CD$_2$Cl$_2$): 7.62 (t, 8 Hz, 2H), 7.36 (d, 8.0 Hz, 1H), 7.22-7.27 (m, 3H), 7.15 (t, 8.0 Hz, 2H), 7.06 (br s, 1H), 6.98-7.01 (m, 1H), 6.90 (dd, 8 Hz, 3.6 Hz, 1H), 6.73 (d, 8 Hz, 1H), 6.52 (d, 8 Hz, 1H), 450-4.55 (m, 2H), 4.05-4.09 (m, 8H), 4.01 (d, 4 Hz, 1H), 3.69-3.72 (m, 2H), 3.38-3.41 (p, 6.4 Hz, 2H), 3.27-0.99 (unidentified peaks). $^{13}$C-NMR (CD$_2$Cl$_2$): 169.4, 169.0, 168.6, 168.5, 158.9, 158.4, 145.9, 142.1, 138.3, 136.5, 130.6, 129.6, 124.7, 124.3, 123.2, 122.8, 119.2, 118.02, 117.3, 115.8, 89.4, 88.6, 88.2, 71.5, 71.3, 71.1, 71.05, 70.9, 69.7, 68.5, 66.6, 65.6, 64.7, 52.8, 51.9, 46.2, 45.6, 44.3, 42, 39.1, 38.7, 38.4, 34.5, 31.5, 22.6, 22.6, 15.04, 13.8. MS (ESI)-TOF observed: 881.4440 (M+H)$^+$, required for $C_{48}H_{60}N_6O_{10}$ 880.4449.

N$^1$-(5-(2-(2-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamido)pentyl)-N$^5$-methylglutaramide (5)

A solution of carboxylic acid 15 (0.053 g, 0.363 mmol, 1.1 eq), HOBt (0.049 g, 0.363 mmol, 1.1 eq), DCC (0.075 g, 0.363 mmol, 1.1 eq) in DMF (0.5 mL) was stirred for 30 min. Amine 14c (0.165 g, 0.330 mmol, 1.0 eq) was added in one portion, and the reaction mixture was stirred under $N_2$ at it for 72 h. The DCU precipitate was collected by vacuum filtration and the filtrate was added to ethyl ether (100 mL) to facilitative precipitation of the crude product. The product was collected by vacuum filtration and washed successively with diethyl ether (50 mL) and n-hexanes (50 mL). Further purification by flash chromatography (silica gel, $CH_2Cl_2$/MeOH/NH$_4$OH, 95/4/1, v/v/v) gave a yield of 0.083 g (40.3%); mp. 77° C. (softens); 89° C. (melts); $^1$H NMR (400 MHz, DMSO-d6) δ 8.94 (br, s, 1H), 8.07-7.99 (m, 3H), 7.55 (d, 8.4 Hz, 1H), 6.58 (d, 8.4 Hz, 1H), 6.48 (d, 8.1 Hz, 1H), 4.81 (br, s, 1H), 4.47 (d, 3.9 Hz, 1H), 4.83-4.31 (m, 1H), 3.98 (s, 2H), 3.96 (d, 3.0 Hz, 2H), 3.12-3.01 (m, 511), 2.77-2.72 (d, 1H), 2.64 (d, 4.5 Hz, 3H), 2.55 (d, 1H), 2.40-2.37 (m, 1H), 2.29 (s, 3H), 2.19-2.09 (m, 2H), 1.64-1.52 (m, 1H), 1.47-1.23 (m, 9H), 1.00-0.86 (m, 1H); HR-FAB MS m/z 632.3294 (M+1)$^+$, required for $C_{31}H_{45}N_5O_9$ 631.3217.

N-methyl-2-(1-(3-((6-methylpyridin-2-yl)ethynyl)phenoxy)-4,8,14-trioxo-6-oxa-3,9,13-triazapentadecan-15-yloxy)acetamide (6)

To the mixture of acid 11 (freshly prepared!, 0.225 g, 0.610 mmol, 1.10 eq), a mixture of HBTU (0.421 g, 1.11 mmol, 2.0 eq) and HOBt solution (2.22 mL of 0.5M HOBt solution in DMF, 1.11 mmol, 2.0 eq) was added at it and stirred for 20 min. To this resulting precipitated solution, a solution of amine 16 (0.133 g, 0.555 mmol, 1.0 eq) dissolved in a solvent mixture of Hunig base/DMF (6 mL, 1/11, v/v) was added. This transparent light brown solution was allowed to stir at it for 17 h. The solvent was removed in vacuum and further purification of the crude product over silica gel column chromatography using the solvent mixture ($CH_2Cl_2$/MeOH/NH$_4$OH, 92/7.5/0.5, v/v/v) gave 0.185 g (60%) the final product 6. $^1$H NMR (400 MHz, CDCl$_3$) δ 7.54-6.96 (m, 8H), 4.06 (m, 2H), 4.01 (s, 2H), 3.96 (s, 2H), 3.92 (s, 2H), 3.89 (s, 2H), 3.60-3.2 (m, 6H), 2.67 (d, 4.8 Hz, 3H), 2.49 (s, 3H), 1.33 (m, 2H). $^{13}$C NMR (100 MHz) δ 169.57, 169.35, 169.16, 169.07, 168.99, 158.75, 158.16, 142.04, 136.86, 129.63, 124.65, 124.53, 123.12, 117.45, 116.08, 115.96, 88.77, 88.34, 70.36, 66.25, 55.0, 42.99, 38.29, 25.52, 24.25, 18.39, 16.97, 12.45. MS (ESI)-TOF observed 554.3867 (M+1), 576.3735 (M+Na$^+$), required for $C_{28}H_{35}N_5O_7$ 553.2536.

(5α,6α)-6-Amino-4,5-Epoxy-3,14-dihydroxy-17-methylmorphinan[α-Oxymorphamine] (7)

The benzyl-protected α-oxymorphamine was dissolved in methanol (150 mL) and transferred to a Parr bottle (250 mL) containing a suspension of Pearlman's catalyst (20% Pd(OH)$_2$/C) (2.0 g, 25% by wt of substrate) in methanol (20 mL). The reaction was carried out at 70 PSI (H$_2$ gas) on the Par apparatus for 38 h, at which time TLC (D/M/A, 89/10/1, v/v/v) showed the complete disappearance of starting material. The reaction mixture was filtered over Celite and the solvent was removed in vacuum to give a crude product. Purification by flash chromatography (silica gel, starting with $CH_2Cl_2$/MeOH/NH$_4$OH 94.5/5/0.5, v/v/v and switching to $CH_2Cl_2$/MeOH/NH$_4$OH, 89/10/1, v/v/v, midway through) gave 7.52 g (70.5% yield over the last three steps) of amine; R$_f$=0.1 (silica gel, D/M/A. 89/10/1. v/v/v). $^1$H NMR (400 MHz, D$_2$O-d$_2$) δ 6.77 (d, 8.4 Hz, 1H), 6.83 (d, 8.4 Hz, 1H), 4.81 (d, 3.9 Hz, 1H), 3.81 (t, 4.2 Hz, 1 Hz), 3.77 (d, 3.9 Hz, 1H), 3.59 (d, 6.9 Hz, 1H), 3.20-2.79 various un resolved peaks, 2.42 (m, 1H), 1.03 (m, 1H). HR-FAB MS/$C_{17}H_{22}N_2O_3$ [M+H]$^+$, calcd. 302.16304. found 302.1683.

2-(2-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetic acid (8)

Diglycol anhydride (0.96 g, 8.267 mmol, 1.0 eq) was added (as a solid) in one portion to a stirred solution of α-oxymorphamine (7) (2.50 g, 8.267 mmol, 1.0 eq) in THF (110 mL). The flask was sealed with a septum and was stirred at rt for 18 h. The product was then collected by filtration and washed with THF to afford 3.00 g (86.7%) of the acid; mp>260° C.; $^1$H NMR (400 MHz, DMSO-d$_6$) δ 8.66 (d, 8.1 Hz, 1H), 6.56 (d, 7.8 Hz, 2H), 6.50 (d, 7.8 Hz, 2H), 4.45 (d, 4.2 Hz, 1H), 4.37-4.28 (m, 1H), 3.92 (d, 1.5 Hz, 2H), 3.90 (d, 1.8 Hz, 2H), 3.15 (s, 1H), 2.79-2.72 (m, 1H), 2.49-2.39 (m, 5H), 2.33-2.23 (m, 2H), 1.65-1.60 (m, 1H), 1.48 (d, 10.8 Hz, 1H), 1.34-1.27 (m, 2H), 0.89-0.80 (m, 1H).

2-((3-(2-azidoethoxyl)phenyl)ethynyl)-6-methylpyridine (9)

Added 5.5 mL of dry MeCN to a mixture of 3-hydroxy-MPEP (2a) (0.333 g, 1.59 mmol) and K$_2$CO$_3$ (1.1 g, 7.955 mmol) and allowed to react at room temperature for 40 min. To the light yellow slurry was added 2-azidoethyl 4-methylbenzenesulfonate (39) (0.576 g, 2.387 mmol) solution in MeCN (3 mL). The reaction was allowed to stiff at room temperature for 5 min. and then heated to 70° C. until TLC analysis indicated consumption of starting material (about 5 h). The reaction was allowed to cool to room temperature and concentrated in vacuum. The slurry obtained was added water and extracted with EtOAc (4×25 mL), dried over anhydrous $MgSO_4$, concentrated in vacuum to provide crude product which was further purified by column chromatography using EtOAc:Hex (1:5) to provide 0.414 g (93%) of 9 brown oil; $^1$H NMR (400 MHz, $CDCl_3$) δ 7.58 (t, J=8.0 Hz, 1H), 7.36 (d, J=8.0 Hz, 1H), 7.22-7.30 (m, 2H), 7.15-7.16 (m, 1H), 7.12 (d, J=8.0 Hz, 1H), 6.94-6.97 (m, 1H), 4.16 (t, J=4.0 Hz, 2H), 3.61 (t, J=4.0 Hz, 2H), 2.59 (s, 3H).

2-(3-((6-methylpyridin-2-yl)ethynyl)phenoxy)ethanamine (10)

To a solution of azide 9 (0.147 g, 0.528 mmol) in 2.5 mL THF was added $PPh_3$ (0.208 g, 0.792 mmol) and 0.5 mL of water. Evolution of gas resulted and the reaction mixture was allowed to stir at room temperature over night. The reaction mixture was concentrated in vacuum, re-dissolved in EtOAc and passed through short $SiO_2$ column (length=15 cm., diameter=2.5 cm) while first washing with EtOAc to remove by-products and then with ($CH_2Cl_2$/MeOH/$NH_4OH$, 89/10/1, v/v/v). The fractions containing the desired product are dried over anhydrous MgSO4, concentrated in vacuum to provide 0.110 g (86%) of 10 as light yellow oil. $^1$H NMR (400 MHz, $CD_3OD$) 7.65 (t, 7.6 Hz, 1H), 7.37 (d, 7.6, 1H), 7.27 (t, 8.4 Hz, 1H), 7.14-7.21 (m, 3H), 6.98-7.00 (m, 1H), 3.99 (t, 5.2 Hz, 2H), 2.99 (t, 5.3 Hz, 2H), 2.49 (s, 3H). $^{13}$C NMR (100 MHz) 160.19, 160.05, 143.14, 138.64, 130.84, 125.73, 125.55, 124.41, 124.33, 118.50, 117.20, 90.16, 89.01, 70.44, 41.75, 23.91.

2-(2-(2-(3-((6-methylpyridin-2-yl)ethynyl)phenoxy)ethylamino)-2-oxoethoxy)acetic acid (11)

To a mixture of amine 10 (0.362 g, 1435 mmol) and commercially available diglycolic anhydride (0.172, 1.435 mmol) was added in THF (15 ml, 0.1 M). After 2 h. the TLC analysis indicated completion of reaction. Removal of solvent under reduced pressure, followed by purification of crude product on silica gel chromatography (THF/MeOH, 1/4, v/v) provided 0.5 g (95%) of acid 11 as yellow fluffy solid. $^1$H NMR (400 MHz, $CD_3OD$) 7.75 (t, 8 Hz, 1H), 7.34 (d, 7.6 Hz, 1H), 7.18-7.24 (m, 2H), 7.07-7.09 (m, 2H), 6.92-6.95 (m, 1H), 4.09 (s, 2H), 4.02 (t, 5.6 Hz, 2H), 3.99 (s, 2H), 3.57 (t, 5.6 Hz, 2H), 2.44 (s, 3H).

2,2-dimethyl-4,9-dioxo-3,11-dioxa-5,8-diazatridecan-13-oic acid (12a)

To a colorless/transparent solution of glycolic anhydride (0.44 g, 3.67 mmol, 1.0 eq) in THF (6 mL) at −50° C. was added tert-butyl(2-aminoethyl)carbamate (40) (0.581 ml, 0.588 g, 3.67 mmol, 1.0 eq) dropwise. The cold bath was removed and the reaction was allowed to stir at rt for 20 h. The solvent was removed to provide 12a as a white solid (0.985 g, 97% yield). MS (ESI)-TOF (negative) observed 275.1636 (M−1), required exact mass 276.1321.

2,2-dimethyl-4,12-dioxo-3,14-dioxa-5,11-diazahexadecan-16-oic acid (12c)

To a colorless/transparent solution of glycolic anhydride (0.3 g, 3.26 mmol, 1.0 eq) in THF (6 mL) at −50° C., tert-butyl (5-aminopentyl)carbamate (0.7 ml, 0.66 g, 3.26 mmol, 1.0 eq) was added dropwise. The cold bath was removed and the reaction was allowed to stir at rt for 21 h. The solvent was removed in vacuum to provide 12c as light yellow oil (1.038 g, quant. yield). $^1$H NMR (400 MHz, DMSO-$d_6$) δ 7.80 (t, 5.6 Hz, 1H), 6.73 (t, 5.6 Hz, 1H), 4.07 (s, 2H), 3.93 (s, 2H), 3.06 (dd, 13.2 Hz, 6.8 Hz, 2H), 2.87 (dd, 13.0 Hz, 6.8 Hz, 2H), 1.35 (s, 9H), 1.14-1.23 (m, 2H). $^{13}$C NMR (100 MHz) δ 171.49, 168.58, 155.59, 77.32, 70.19, 67.90, 38.10, 29.16, 28.82, 28.28, 23.67. MS (ESI)-TOF (negative) observed 317.2211 (M−1), required for $C_{10}H_{22}N_2O_2$ 318.1791.

3,13-dioxo-1-phenyl-2,15-dioxa-4,12-diazaheptadecan-17-oic acid (12d)

Mono-Cbz protected heptadiamine 1,7 (2.59 g, 0.98 mmol) and glycolic anhydride (1.14 g, 0.98 mmol) were mixed in 200 mL anhydrous THF, and stirred overnight at room temperature. Next day, the precipitate that formed was filtered, and filtrate dried in vacuum. Yield: 70%. $^1$H-NMR ($d_6$-DMSO)=7.8 (m, 1H), 7.3-7.2 (m, 5H), 7.1 (m, 1H), 4.9 (s, 2H), 4.0 (s, 2H), 3.9 (s, 2H), 3.0-2.9 (m, 4H), 1.4-1.2 (m, 10H).

tert-butyl(2-(2-(2-(((4aS,7S,7aR,12bS)-4a,9-dihydroxy-3-methyl-2,3,4,4a,5,6,7,7a-octahydro-1H-4, 12-methanobenzofuro[3,2-e]isoquinolin-7-yl) amino)-2-oxoethoxy)acetamido)ethyl)carbamate (13a)

To a solution of acid 12a (0.550 g, 1.984 mmol, 1.5 eq) in DMF (1 ml) and $CH_2Cl_2$ (12 mL) was added EEDQ (0.496 g, 1.984 mmol, 1.5 eq) and stirred for 15 min. To this solution α-oxymorphamine (7) (0.4 g, 1.323 mmol, 1.0 eq) in $CH_2Cl_2$ (3 mL) was added. After 4 h., TLC analysis indicated completion of the reaction. The solvent was removed in vacuum and the crude product was purified over silica gel column chromatography using $CH_2Cl_2$ (100%), and then the mixture ($CH_2Cl_2$/MeOH/$NH_4OH$, 95/4/1, v/v/v). The final product 13a was isolated as light brown amorphous solid (0.684 g, 92% yield). $^1$H NMR (400 MHz, $CDCl_3$) δ 7.36 (br d, 8.0 Hz, 1H), 7.27 (br s, 1H), 6.63 (d, 8.0 Hz, 1H), 6.46 (d, 8.0 Hz, 1H), 5.55 (br s, 1H), 4.41-4.46 (m, 2H), 3.96-4.03 (m, 4H), 3.20-3.35 (m, 4H), 3.04 (br d, 19.0 Hz, 1H), 2.70 (d, 6.0 Hz, 1H), 2.48-2.53 (dd, 12 Hz, 6.4 Hz, 1H), 2.26 (s, 3H), 2.14-2.34 (m, 3H), 1.63-1.72 (m, 1H), 1.46-1.56 (m, 2H), 1.34 (s, 9H), 0.85-0.96 (m, 1H). $^{13}$C NMR (100 MHz) δ 169.61, 168.07, 157.53, 145.54, 138.16, 130.79, 125.37, 119.30, 117.49, 89.26, 79.95, 76.89, 71.03, 70.78, 69.57, 64.57, 46.41, 45.66, 44.77, 43.08, 39.86, 39.69, 33.24, 29.15, 28.30, 22.03, 21.31. MS (ESI)-TOF observed 583.2337 (M+Na), required for $C_{28}H_{40}N_4O_8$ 560.2846.

tert-butyl(3-(2-(2-(((4aS,7S,7aR,12bS)-4a,9-dihydroxy-3-methyl-2,3,4,4a,5,6,7,7a-octahydro-1H-4, 12-methanobenzofuro[3,2-e]isoquinolin-7-yl) amino)-2-oxoethoxy)acetamido)propyl)carbamate (13b)

Acid 12b was generated instantly and without isolation utilized. To a 25 mL flame dried round bottom flask, glycolic anhydride (0.069 g, 0.594 mmol, 1.1 eq) and THF (1 mL) was added followed by addition of tert-butyl (3-aminopropyl)carbamate (0.107 g, 0.594 mol, 1.1 eq) and stirred at rt for 1.75 h. until TLC indicated completion of the reaction.

To this mixture a solution of α-oxymorphamine (7) (0.173 g, 0.574 mmol, 1.0 eq) in minimum amount of DMF (0.4 mL) and EEDQ (0.213 g, 0.861 mmol, 1.5 eq) was added. The light brown solution was stirred at rt for 17 h. until TLC indicated completion of the reaction. After that the solvent was removed in vacuum to provide crude product which was purified over silica gel column chromatography using EtOAc (100%), and then the mixture ($CH_2Cl_2$/MeOH/$NH_4OH$, 95/5/1 to 90/10/1, v/v/v). The final product 13b was isolated as amorphous off-white solid (0.195 g, 59% yield). $^1H$ NMR (400 MHz, $CDCl_3$) δ 7.63 (t, 6.0 Hz, 1H), 7.55 (d, 5.6 Hz, 1H), 7.37 (s, 1H), 6.7 (d, 8.0 Hz, 1H), 6.52 (d, 8.8 Hz, 1H), 5.57 (br s, 1H), 4.52-4.57 (m, 2H), 4.02-4.07 (m, 4H), 3.35-3.37 (m, 2H), 3.10-3.14 (m, 3H), 2.77 (d, 6.4 Hz, 1H), 2.56 (dd, 18.4 Hz, 6.4 Hz, 1H), 2.19-2.42 (m, 3H), 2.34 (s, 3H), 1.70-1.76 (m 3H), 1.53-1.59 (m, 2H), 1.42 (s, 9H), 1.41 (m, 1H), 0.99-1.10 (m, 1H). $^{13}C$ NMR (100 MHz) δ169.32, 168.21, 156.38, 145.61, 138.14, 130.37, 124.80, 118.90, 117.73, 88.91, 78.84, 71.07, 70.90, 69.38, 64.27, 46.10, 45.60, 44.49, 42.79, 37.16, 35.94, 33.03, 29.37, 28.83, 28.30, 21.74, 20.83. MS (ESI)-TOF observed 575.3625 (M+1), 597.3467 (M+$Na^+$), required for $C_{29}H_{42}N_4O_8$ 574.3003.

tert-butyl(5-(2-(2-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamido)pentyl)carbamate (13c)

To a solution of acid 12c (0.630 g, 1.984 mmol, 1.5 eq) in $CH_2Cl_2$ (6 mL) was added EEDQ (0.496 g, 1.984 mmol, 1.5 eq) and stirred for 10 min. followed by addition of a solution of α-oxymorphamine (7) (0.4 g, 1.323 mmol, 1.0 eq) in THF (3 mL). After 4.5 h., TLC analysis indicated completion of the reaction. Then, the solvent was removed in vacuum and the crude product was purified over silica gel column chromatography using $CH_2Cl_2$ (100%), and then the solvent mixture ($CH_2Cl_2$/MeOH/—$NH_4OH$, 95/4/1, v/v/v). The final product 13c was isolated as light brown amorphous solid (0.705 g, 88% yield). $^1H$ NMR (400 MHz, $CDCl_3$) δ 7.37-7.35 (br d, 7.6 Hz, 1H), 7.25 (s, 1H), 6.76 (d, 8 Hz, 1H), 6.67 (t, 6 Hz, 1H), 6.54 (d, 8.0 Hz, 1H), 4.72 (br s, 1H), 4.58 (br s, 2H), 4.02-4.13 (m, 4H), 3.30-3.37 (m, 2H), 3.10-3.14 (m, 3H), 2.78, (d, 7.0 Hz, 1H), 2.57 (dd, 18 Hz, 8 Hz, 1H), 2.20-2.41 (m, 3H), 2.34 (s, 3H), 1.58-1.80 (m, 1H), 1.37-1.60 (m, 9H), 1.45 (s, 9H), 1.24-1.27 (m, 1H), 0.94-1.05 (m, 114). $^{13}C$ NMR (100 MHz) δ 169.11, 168.27, 156.29, 149.44, 138.07, 130.59, 125.16, 119.08, 117.59, 89.26, 79.10, 71.22, 71.07, 69.47, 64.39, 60.21, 46.25, 45.59, 44.60, 42.94, 39.85, 39.06, 33.18, 29.37, 29.02, 28.51, 28.26, 23.53, 21.88, 21.02, 20.86.

N-(2-aminoethyl)-2-(2-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamide (14a)

To a cold (0° C.) solution of protected amine 13a (0.684 g, 1.220 mmol, 1.0 eq) in 15 mL of $CH_2Cl_2$ was added dropwise trifluoroacetic acid (2.225 g, 1.50 mL, 19.52 mmol, 16.0 eq). The reaction was allowed to warm to rt and stirred for 2.5 h. at which point TLC indicated completion of reaction. The solvent was removed in vacuum. The resulting light yellow oil was re-dissolved in $CH_2Cl_2$ (15 mL) and cooled to 0° C. To this oil excess HCl-ether solution (2.44 mL, 2M solution, 4.88 mmol, 4.0 eq) was added dropwise to give a precipitated solution which was stirred for 0.5 hour. The reaction was concentrated in vacuum to provide a white solid which upon triturating with ether (under $N_2$) provided off-white solid. This solid was treated with $CH_2Cl_2$ (4 mL) followed by ether (15 mL) and the precipitate 14a was filtered. The process was repeated twice and the resulting solid was filtered off to give 14a as white solid (0.651 g, 100% yield). $^1H$-NMR (DMSO-$d_6$): δ 9.1 (s(br), 1H), 8.5 (s, 1H), 6.5 (AB, $J_{AB}$=7.9 Hz, 2H), 5.7 (s, 1H), 5.0 (s, 1H), 4.7 (s, H), 4.35 (s(br), 2H), 4.0-1.0 (m, unresolved peaks). MS (ESI)-TOF observed 461.2322 $(M+1)^+$, required for $C_{23}H_{32}N_4O_6$ 460.2322.

N-(3-aminopropyl)-2-(2-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamide (14b)

To a cold (0° C.) solution of protected amine 13b (0.195 g, 0.339 mmol, 1.0 eq) in 4 mL of $CH_2Cl_2$, trifluoroacetic acid (0.465 g, 0.420 mL, 4.071 mmol, 16.0 eq) was added dropwise. The reaction was allowed to warm to rt and stirred for 6 h. at which point TLC indicated completion of the reaction. The solvent was removed in vacuum. The resulting light yellow oil was re-dissolved in $CH_2Cl_2$ (3 mL) and cooled to 0° C. To this oil, excess of HCl-ether solution (2 mL, 2M solution) was added dropwise to give a precipitated solution which was stirred for 10 h. Thereafter, the reaction was concentrated in vacuum to provide an off-white solid which upon triturating twice with ether followed by filtration provided 14b as off-white solid (0.173 g, quant. yield). $^1H$ NMR (400 MHz, $CD_3OD$) δ 6.69 (d, 8.0 Hz, 1H), 6.59 (d, 8.0 Hz, 1H), 4.61-4.62 (m, 1H), 4.49-4.53 (m, 1H), 4.02 (s, 2H), 4.01 (s, 2H), 3.60 (d, 5.6 Hz, 1H), 3.23-3.43 (m, 4H), 3.04 (dd, 20 Hz, 6 Hz, 1H), 2.92 (t, 7.2 Hz, 2H), 2.86 (s, 3H), 2.51-2.56 (m, 1H), 1.75-1.86 (m, 3H), 1.56-1.63 (m, 2H), 1.43-1.48 (m, 1H), 1.01-1.11 (m, 1H). $^{13}C$ NMR (100 MHz) δ 172.53, 171.15, 147.11, 140.26, 129.88, 123.44, 121.01, 119.65, 89.06, 71.46, 71.10, 68.07, 63.70, 53.68, 47.82, 46.67, 42.12, 38.31, 36.70, 31.57, 30.20, 28.54, 25.11, 20.90, 9.42. MS (ESI)-TOF observed 475.2891 (M+1), 497.2708 (M+$Na^+$), required for $C_{24}H_{34}N_4O_6$ 474.2478.

N-(5-aminopentyl)-2-(2-(((4aS,7S,7aR,12bS)-4a,9-dihydroxy-3-methyl-2,3,4,4a,5,6,7,7a-octahydro-1H-4,12-methanobenzofuro[3,2-e]isoquinolin-7-yl)amino)-2-oxoethoxy)acetamide (14c)

To a cold (0° C.) solution of protected amine 13c (0.705 g, 1.170 mmol, 1.0 eq) in 15 mL of $CH_2Cl_2$, trifluoroacetic acid (2.96 g, 2.00 mL, 25.96 mmol, 22.0 eq) was added dropwise. The reaction was allowed to warm to rt and stirred for 2 h. at which point TLC indicated completion of the reaction. Then, the solvent was removed in vacuum. The resulting light yellow oil 14c was re-dissolved in $CH_2Cl_2$ (10 mL) and cooled to 0° C. To this oil, excess of HCl-ether solution (2 mL, 2M solution) was added dropwise to give a precipitated solution, which was stirred for 4 h. The reaction mixture was concentrated in vacuum to provide a white solid which upon triturating twice with ether (overnight under $N_2$) followed by filtration provided 14c as amorphous white solid (0.622 g, 92% yield). MS (ESI)-TOF observed 503.3018 (M+1), required for $C_{26}H_{38}N_4O_6$ 502.2791.

N-(7-aminoheptyl)-2-(2-(((4aS,7S,7aR,12bS)-4a,9-dihydroxy-3-methyl-2,3,4,4a,5,6,7,7a-octahydro-1H-4, 12-methanobenzofuro[3,2-e]isoquinolin-7-yl)amino)-2-oxoethoxy)acetamide (14d)

Acid 12d (780 mg, 2 mmol, 1 eq), α-oxymorphamine (3) (614 mg, 2 mmol, 1 eq), and EEDQ (520 mg, 2.1 mmol)

were mixed in 10 mL methylene chloride and stirred overnight. The next day, solvent was evaporated. Afterwards, the material was hydrogenated in methanol mediated by Pd/C (10%) (cat.) and 1,4-cyclohexadiene. Yield: 852 mg (76.7%).

Methylaminocarbonylmethoxy-acetic acid (15)

To diglycolic anhydride (5.0 g, 43.08 mmol, 1 eq) a 2M THF solution of methylamine (25 mL, 43 mmol) was added in two portions. After 18 h the reaction mixture was concentrated in vacuum to afford crude 15 as oil (41). After removal of solvent under high vacuum (24 h) the product crystallized to give 6.34 g of 15; 57° C.; $^1$H NMR (DMSO-d$_6$) δ 12.76 (s(br), 1H), 7.78 (s(br), 1H), 4.08 (s, 2H), 3.93 (s, 2H), 2.61 (d, 4.8 Hz, 3H); $^{13}$C NMR (DMSO-d$_6$) δ 172.2, 170.0, 71.0, 69.5, 25.8, 25.0 tert-butyl 3-(2-(2-(methylamino)-2-oxoethoxy)acetamido)propylcarbamate (16a)

To a solution of acid 15 (0.38 g, 2.58 mmol, 1.5 eq) dissolved in CH$_2$Cl$_2$/THF (8 mL, 1/1, v/v), EEDQ (0.64 g, 2.58 mmol, 1.5 eq) dissolved in DMF (0.2 mL) was added and stirred for 10 min. To this transparent solution, a solution of N-Boc-diaminopropane (0.3 g, 1.72 mmol, 1.0 eq) dissolved in THF (2 mL) was added. After 5.5 h., TLC analysis indicated completion of the reaction. The solvent was removed in vacuum and the crude product was purified over silica gel column chromatography using the solvent mixture (CH$_2$Cl$_2$/MeOH/NH$_4$OH, 95/4/1, v/v/v). The final product 16a was isolated as light yellow amorphous solid (0.337 g, 65% yield). $^1$H NMR (400 MHz, CDCl$_3$) δ 7.66 (br s, 1H), 7.30 (br s, 1H), 5.61 (br s, 1H), 3.79 (s, 2H), 3.76 (s, 2H), 3.06-3.07 (m, 2H), 2.92-2.94 (m, 214), 2.55 (d, 4.4 Hz, 3H), 1.36 (m, 2H), 1.17 (s, 9H). $^{13}$C NMR (100 MHz) δ 168.79, 168.07, 156.62, 78.51, 69.95, 35.98, 34.08, 29.12, 27.78, 25.13.

N-(3-aminopropyl)-2-(2-(methylamino)-2-oxoethoxy)acetamide hydrochloride (16)

To a cold (0° C.) solution of protected amine 16a (0.337 g, 1.11 mmol, 1.0 eq) in 6 mL of CH$_2$Cl$_2$, trifluoroacetic acid (2.03 g, 1.37 mL, 1.77 mmol, 16.0 eq) was added dropwise. The reaction was allowed to warm to rt and stirred for 2 h. at which point TLC indicated completion of the reaction. The solvent was removed in vacuum. The resulting light brown oil was re-dissolved in DCM (10 mL) and cooled to 0° C. To this oil, ac excess of HCl-ether solution (0.666 mL of 2M solution, 13.32 mmol. 1.2 eq) was added dropwise which was stirred for 15 h. Then, the reaction was concentrated in vacuum to provide an oily product which upon triturating twice with ether followed by filtration in vacuum provided 16 as off-white semi solid (0.266 g, quant. yield).

Example 2: Biological Evaluation

The bivalent ligands (3, 4a-4d) contain pharmacophores derived from the mu opioid agonist, oxymorphone, and the mGluR$_5$ antagonist, m-methoxy-MPEP (M-MPEP) (Gasparini F, et al., *Bioorg. Med. Chem. Lett.*, 2002, 407-409). The results below show that in LPS pretreated mice and in C3H mice, the antinociceptive potency of i.t.-administered members of the series is dependent upon spacer length, with compound 4c (22 atoms) having unprecedented potency without tolerance.

Materials and Methods

Animals:

Male ICR-CD1 mice (17-25 g; Harlan, Madison, Wis.), or male C3H mice (15-20 g, National Cancer Institute, Bethesda, Md.) are housed in groups of 4 in a temperature- and humidity-controlled environment with unlimited access to food and water. They are maintained on a 12 h light/dark cycle. All experiments are approved by the Institutional Animal Care and Use Committee of the University of Minnesota (Minneapolis, Minn.).

Drug Administration:

Compounds were dissolved in 10% DMSO and then diluted to less than 1% DMSO in the test solutions. DMSO when given i.c.v. or i.t. in a 1% or less concentrated solution did not show any antinociception. Compounds were administered in a 5-μl volume in conscious mice, either i.c.v. (Haley T J & McCormick W G, *Br J Pharmacol Chemother*, 1957, 12(1), 12-15) or i.t. (Hylden J L K & Wilcox G L, *Eur. J. Pharmacol.*, 1980, 67(2-3), 313-316). Peak times were determined by comparing the percent maximal possible effect (% MPE) at 5, 10, 20 and 60 minutes after injection.

Pain Models:

Three pain models were used in the study. LPS was used in the tail Flick assay and respiration studies. CFA was used with mechanical hypersensitivity and rota-rod assays. Mechanical hypersensitivity was also used in the bone tumor model.

The first group mice were pretreated with lipopolysaccaride (LPS, 1 mg/kg, i.p. from *Escherichia coli* 0111:B4; Sigma-Aldrich, St. Louis, Mo.) for 24 hours before testing for antinociception of compounds 2-6 (Seo Y-J, et al., *Pharmacol., Biochem. Behav.*, 2008, 91, 121-127). This group was compared to a group without pretreatment.

The complete Freund's adjuvant (CFA) was the second pain model used to measure antinociception in the behavioral studies. The left hindpaws were injected (intraplantar) with a 50% solution of CFA (10 μg, Sigma-Aldrich) in PBS while the mice were under isoflurane anesthesia. Forty-eight hours after the paws were injected antinociception was measured for the test compounds (Sorge R E, et al., *J Neurosci.*, 2011, 31(43), 15450-15454).

The mouse hind paw model of bone cancer was the third model of pain (Wacnik P W, et al., *Pain Research & Management*, 2000, 16, 615-637; and Wacnik P W, et al., *J Neurosci*, 2001, 21(23), 9355-9366). *Cell Culture*: National Collection of Type Cultures (NCTC) clone 2472 fibrosarcoma cells, originally derived from a connective tissue tumor in a C3H mouse, were obtained from the American Type Cell Culture Collection (Rockville, Md.). Cells were grown and maintained in accordance with standard cell culturing techniques. NCTC cells were grown to 80-90% confluence in 75 cm$^2$ flasks (Corning, Lowell, Mass.) in Dulbecco's Modification of Eagles Medium (Invitrogen, Carlsbad, Calif.) fortified with 10% Horse Serum and sodium bicarbonate. Cell cultures were housed in a water-jacketed incubator with 5% carbon dioxide at 37° C.

Cells were prepared for implantation by first pouring off the culture medium and washing with phosphate-buffered saline (PBS). Trypsin was added to flask and placed in incubator for 3 minutes. Upon detachment, cells were suspended in an ample amount of culture medium to terminate enzymatic activity and centrifuged for 10 min at 1000 g. Fibrosarcoma cells were re-suspended in a known amount of PBS for counting, quantified on a hemacytometer, pelleted and re-suspended in PBS. Fibrosarcoma cells were again re-suspended to a final concentration of 2×10$^5$ cells in 20 μl. Initially, animals were anesthetized in a plexi-glass chamber using 3% isoflurane in 3 L/min oxygen. Once each mouse was completely anesthetized, a maintenance rate of 2% isoflurane in 1.5 L/min oxygen was maintained during the short implantation procedure. Tumor cells were manually injected by boring into the calcaneus bone using a 29½ gauge needle connected to a sterile 0.3 ml insulin syringe as previously described (19). Following injection, mice were allowed to recover in cages on a heating pad. Animals showing any signs of dysfunction (e.g. problems with ambulation, lethargy or excessive bleeding) or distress where euthanized according to CO2 guidelines.

Assays

Radiant Tail Flick:

The tail flick assay is used first to test for antinociception as described by D'Amour and Smith (D'AMOUR FE & SMITH DL (1941) *J. Pharmacol. Exp. Ther.* 72(1):74-79) and modified by Dewey et al. (Dewey W L, Harris L S, Howes J F, & Nuite JA (1970) *J. Pharmacol. Exp. Ther.* 175(2):435-442). For the measurement of the tail-flick latency, mice are wrapped in a light cloth and held gently in one hand with the tail positioned in the apparatus (Tail Flick Analgesia Meter, Columbus Instruments, Columbus, Ohio) for radiant heat stimulus. The tail-flick response is elicited by applying radiant heat to the dorsal side of the tail. The intensity of the heat is set so that the mouse flicks its tail within 2 to 3 seconds. The test latency is measured before drug treatment (control) and again after the drug treatment (test) at the peak time of the compound; a 10 second maximum cut-off time is used to prevent damage to the tail. Antinociception is quantified according to the Harris L S & Pierson A K, *J. Pharmacol. Exp. Ther.*, 1964, 143(2):141-148, as the percent maximal possible effect (% MPE), which is calculated as: % MPE=(Test−Control/10−Control)×100.

Mechanical Hypersensitivity:

C3H mice were was placed under a clean glass cup on a wire mesh grid and allowed to acclimate for thirty minutes. Mechanical hypersensitivity was tested using a von Frey filament #3.61 (which produces a force of 0.7 grams) to the plantar surface of both the left and right hind paw with enough force to cause it to bow slightly. Starting with the right hind paw, the number of positive responses out of a total of 10 applications was recorded followed by the left hind paw. Positive response was indicated by a sharp withdrawal or flinching behavior of the paw. Baseline von Frey measurements were obtained prior to treatment with CFA, tumor and saline controls. Control animals did not differ from untreated mice. Subsequent measurements were taken at various time points after intrathecal (i.t.) injection of test compounds on days 3, 7, 10, 14, 17, and 21. % MPE was calculated ((Time-point value−Day# baseline)/(Day 0 baseline−day# baseline))*100 (Smeester B A, Al-Gizawiy M, & Beitz A J (2012) *Evidence-Based Complementary and Alternative Medicine* 2012:16). Animals with saline injection served as controls for tumor cell implantation and tumor-induced nociception. Behavioral assessments were conducted during the light cycle at approximately the same time each day. The investigator performing the von Frey testing was blinded to the animal and compound injected.

Figure 10:
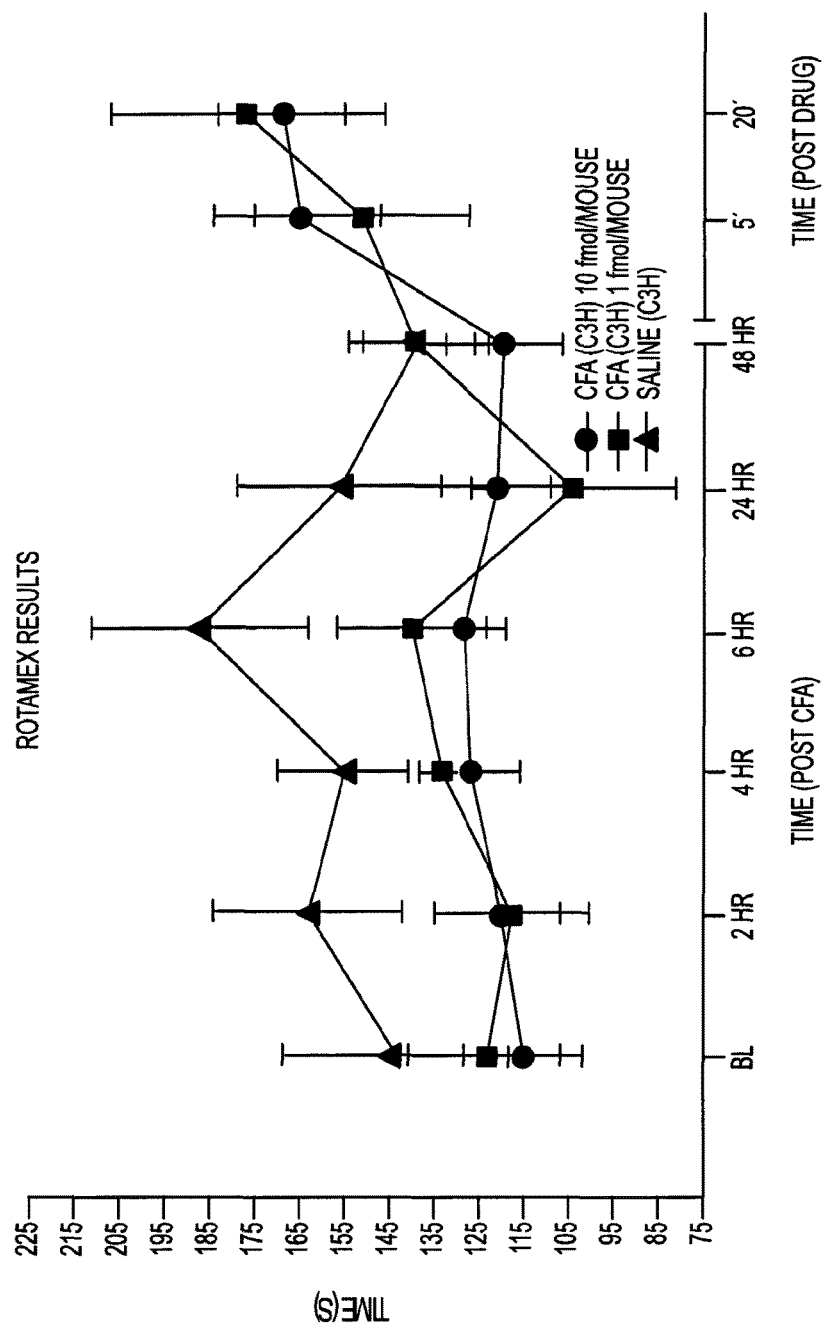
FIG. 10 Illustrates data generated for compound 4c in the Rota-Rod assay described in Example 2.

Rota-Rod:

To first evaluate the effects of CFA injection on motor coordination, a group of 10 animals were tested on the Rotamex (Columbus Instruments Rotamex 4/8 instrument) for performance. Animals were trained three days prior to undergoing 3-5 minute trials on an accelerating rotating rod (0-20 RPMs). Motor performance was evaluated at 2, 4, 6, 24 and 48 hours post injection. Compound 4c was then injected i.t. and the motor performance was evaluated at 5 and 20 minutes. The time to the first fall were recorded and compared with controls (Kovacs K J, et al., *Pain,* 2008, 136, 75-84). The results for compound 4c are illustrated in FIG. 10. After the 48 hour measurement, animals injected with compound 4c stayed on the Rotomex for a longer period of time compared to animals that did not receive compound 4c.

Respiratory Depression:

Respiratory depression was measured in live mice using the Mouse Ox (small animal Oximeter from STARR Life Sciences Corp, Oakmont, Pa.). CollarClip™—(Un-Anesthetized Neck Sensor) for mice was used as the site for measuring the data. Day one of each experiment involved training the animals using a disposable CollarClip™. The collar was left on for approximately one hour. Respiratory depression was considered positive if the $O_2$ saturation decreased from 96-99% to less than 90%. Mice were monitored for a 60-minute period, with measurements 10-20-30 and 60 minutes.

Acute Tolerance:

Acute tolerance utilizing the radiant tail flick assay was measured by comparing the $ED_{80-90}$ dose on day 1 to the same dose measured 24 hours later on the same mouse. For the LPS pretreated mice, no additional LPS was given to the mice for the acute tolerance test. To confirm that the LPS was still accurate after 48 hours, a compound that produced 97% antinociception (compound 4c) was tested 48 hours after the initial LPS injection and the value did not differ from the 24 hour value. However, the effect was less robust 72 hours after the initial LPS injection. Thus confirming that the acute tolerance test was accurate for the LPS pretreated mice.

Statistics:

At least three groups of four to ten mice are used for each dose response curve. $ED_{50}$ values with 95% confidence intervals (C.I.) are computed with GraphPad Prism 4 by using nonlinear regression methods. Ratios were considered significant if the C.I. did not overlap.

Chronic Constriction Injury (CCI) in Mice:

Chronic constriction injury to the sciatic nerve in mice was performed under pentobarbital (36 mg/kg; i.p.) anesthesia using the procedure described by Bennett and Xie (Bennett G J, Xie Y K. A peripheral mononeuropathy in rat that produces disorders of pain sensation like those seen in man. Pain 1988; 33:87-107.) An incision was made just below the right hip bone, parallel to the sciatic nerve. The sciatic nerve was exposed, and three ligatures (4/0 silk) were tied loosely around the nerve distal to the sciatic notch with 1 mm spacing, until a brief twitch in the respective hind limb was observed. Sham operations involved exposure of the right sciatic nerve without ligature.

Mechanical Allodynia (Von Frey Test):

Mechanical allodynia in mice with CCI was measured by using a series of calibrated nylon von Frey filaments (Stoelting, Wood Dale, Ill., USA), ranging from 0.6 to 6 g. Animals were placed in plastic cages with a wire-mesh floor. They were acclimatized to this environment for approximately 5 min prior to testing to allow for behavioral accommodation. The von Frey filaments were applied in ascending order to the midplantar surface of the operated hindpaw through the mesh floor. Each probe was applied to the foot until it just bent. The time interval between consecutive filament administrations was at least 5 s Animals were habituated to both tests for 7 days before surgery, and the pre-surgery baseline was measured one day before ligation of the sciatic nerve.

Results

Rationale for Ligand Design and Chemistry.

Given that 2 is used both as a radioligand and as a selective pharmacologic antagonist for the mGluR$_5$ suggests that the meta-position can serve as the point of attachment for a spacer that links the mGluR$_5$ antagonist pharmacophore (Alagille D, et al., *Bioorg. Med. Chem. Lett.*, 2005, 15, 945-949) to the MOPR agonist pharmacophore. Thus, replacement of the m-methoxy group of 2 with an m-ethoxyethylamine substituent permitted *facile* attachment of the spacer through the amino group to permit synthesis of bivalent ligand 3 and bivalent ligand series 4. Monovalent ligands 5 and 6 were also prepared as controls.

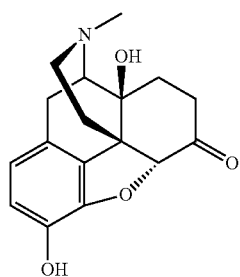

1

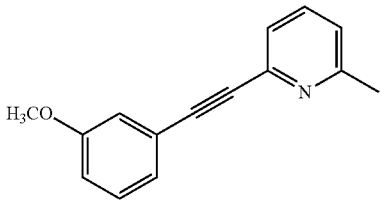

2

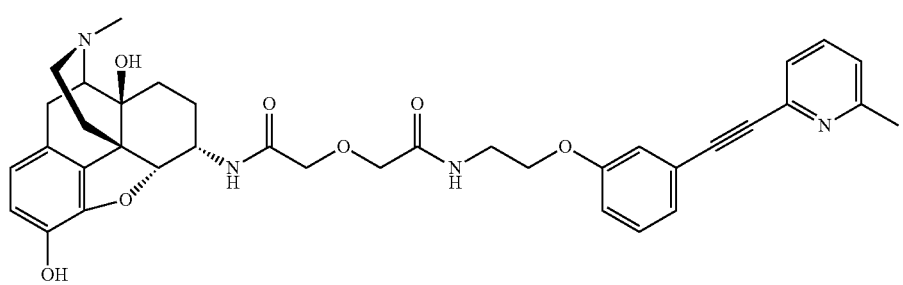

3

(bivalent with shortest spacer!)

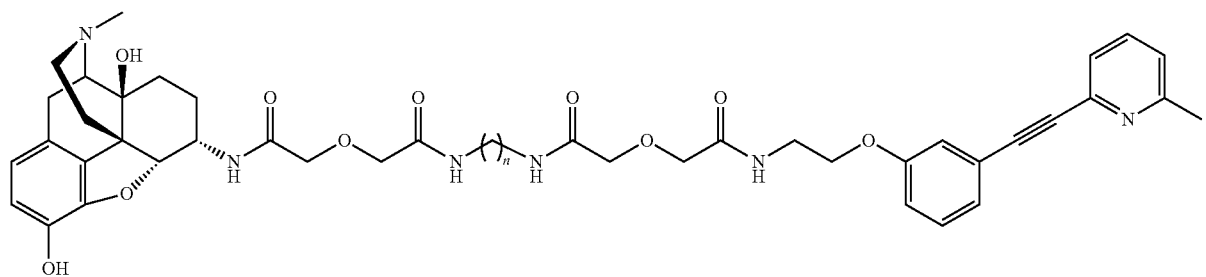

4a (n = 2)
4b (n = 3)
4c (n = 5)
4d (n = 7)

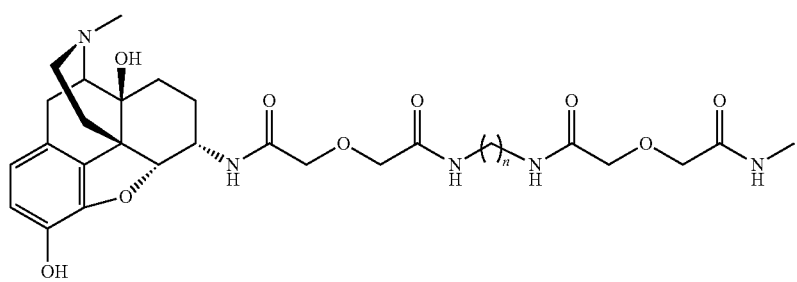

Series 5 (n = 5)

-continued

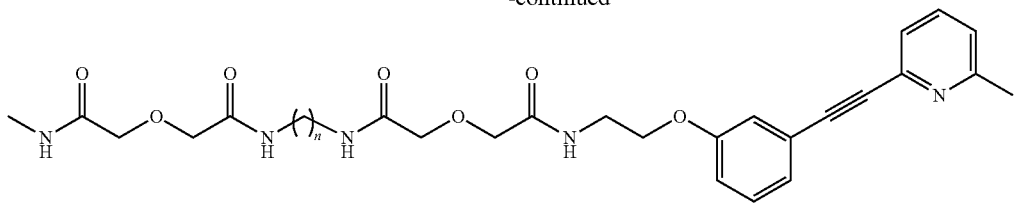

Series 6 (n = 3)

Pharmacophores: oxymorphone (1, MOP agonist), 2 (mGluR$_5$ antagonist, M-MPEP) and target compounds 3, 4a-d, 5, 6.

Pharmacological Results.

Antinociceptive Studies Using Normal and LPS Treated Mice (Table 1).

The bivalent compounds 3, 4a-4d and the monovalents 5 and 6 were tested on LPS treated and untreated (control) mice for their antinociceptive potency using the tail-flick and von Frey assays. In control mice, i.t. administration of compounds 4a-4c were about 3-fold more potent than compound 4d or compound 5. Metabotropic antagonist 6 was about 70-fold less potent than compounds 4a-4c. On the other hand, upon i.c.v. administration, compounds 4a, 4b, and 5 had comparable antinociceptive potencies which were greater than the other ligands. In this mode of administration compound 4c was a partial agonist and compound 4d was 10 fold less potent. Profound differences were observed when mice were pretreated with LPS. The bivalent compound 4c was exceptionally potent (ED$_{50}$=9 fmol/mouse) without tolerance upon i.t. administration. Similar potency without tolerance was also observed in the bone cancer mouse model. The bivalent compounds 4b and 4d were also devoid of tolerance formation with ED$_{50}$ values 10.08 and 0.25 pmol/mouse, respectively, whereas compound 4a created tolerance in this study. Tolerance was also observed upon i.t. administration of bivalent compound 3, with monovalent agonist 5, and with a mixture of compound 5 and antagonist monovalent 6.

TABLE 1

Comparison of the antinociceptive activity of bivalent ligands that contain MOPR agonist/mGluR$_5$ antagonist pharmacophores with corresponding monovalent ligands

| | CONTROLS | | | LPS pretreated (1 mg/kg 24 hours i.p.) | | |
| --- | --- | --- | --- | --- | --- | --- |
| Compound # | ED$_{50}$ (CI) i.t. pmol/mouse | ED$_{50}$ (CI) i.c.v. pmol/mouse | i.c.v./i.t. ratio | ED$_{50}$ (CI) i.t. pmol/mouse | ED$_{50}$ (CI) i.c.v. pmol/mouse | i.c.v./i.t. ratio |
| 2 | 250 pmol/mouse 13.27 ± 3.39% MPE | 250 pmol/mouse 14.59 ± 4.63% MPE | 1 | 250 pmol/mouse 21.96 ± 10.50% MPE | — | — |
| 3 | 114.7 (66.3-198.3) No Tolerance | 529.6 (397.9-704.9) Tolerance | 4.62 | 8.17 (5.90-11.34) Tolerance | 500 pmol/mouse 56.86 ± 8.95% MPE | — |
| 4a | 34.31 (23.47-50.14) Tolerance | 119.50 (76.97-185.4) Tolerance | 3.48 | 20.57 (17.66-23.97) Tolerance | 80.85 (59.08-110.6) Tolerance | 3.93 |
| 4b | 36.08 (25.86-50.33) No Tolerance | 113.3 (74.23-173.0) No Tolerance | 3.14 | 10.08 (4.95-20.52) No Tolerance | 64.36 (42.09-98.42) No Tolerance | 6.38 |
| 4c | 38.70 (25.48-58.77) No Tolerance | 250 pmol/mouse 71 ± 10% MPE No Tolerance | — | 8.83 fmol/mouse (3.02-25.80) No Tolerance | 374.9 (215.6-652.0) 24 hour tolerance Still was 40% MPE | 42,457 |
| 4d | 132.7 (75.77-232.4) No tolerance | 1000 pmol 53.76 ± 16.36% MPE | — | 0.25 (0.13-0.49) No tolerance | 411.9 (274.2-618.6) Tolerance was not measured | 1,648 |
| 5 | 110.06 (81.44-153.16) Tolerance | 89.81 (61.20-126.26) Tolerance | 0.82 | 21.29 (13.55-33.75) Tolerance | 168.9 (124.0-230.2) Tolerance | 1.88 |
| 6 | 2500 pmol/ mouse 26.13 ± 7.27% MPE | 250 pmol/mouse 24.87 ± 11.77% MPE | — | 548.7 (216.1-1394) No tolerance | 2500 pmol/mouse 38.83 ± 11.59% MPE | — |

TABLE 2

Relative potencies of bivalent ligands 3, 4a-d, and 5 + 6 in the LPS- pretreated mice

| | Relative potency |
| --- | --- |
| 3 | 41 |
| 4a | 16 |
| 4b | 33 |
| 4c | 37,700 |

TABLE 2-continued

Relative potencies of bivalent ligands 3,
4a-d, and 5 + 6 in the LPS- pretreated mice

| | Relative potency |
|---|---|
| 4d | 83 |
| (5 + 6)[a] | 1 |

[a]Tested the synergy of the two monovalents (5 and 6); As 5 is 25x more potent than 6, the mixture was 1-part 5 to 25 parts 6. The theoretical $ED_{50}$ was calculated to be 285 pmol/mouse and the observed $ED_{50}$ was 332.9 pmol/mouse (281-396). There was no synergy between the two compounds (22). The potencies are relative to 5 + 6.

The Complete Freund's Adjuvant (CFA) Administration and Antinociception in the Behavioral Studies in Mice.

Recently, Liu et al. used the complete Freund's adjuvant (CFA) to determine $mGluR_5$ receptor contribution to inflammatory tongue pain and determined that mGluR5-pERK signaling is crucial in the development of mechanical and heat hypersensitivity. This study revealed that pERK-immunoreactive cells (IR) are very intensive in upper cervical spinal cord (C1-C2) (Liu M-G, et al., *J Neuroinflammation*, 2012, 258). The left hindpaws of mice were injected (intraplantar) with a 50% solution of CFA (10 μg, Sigma-Aldrich) in PBS while the mice were under isoflurane anesthesia. The antinociceptive studies of these mice are illustrated in FIG. 1. In i.t. administration of compound 4c an $ED_{50}$ of 7.66 fmol/mouse was observed showing effectiveness of this bivalent ligand.

Antinociceptive Studies in Bone Cancer.

Figure 2:
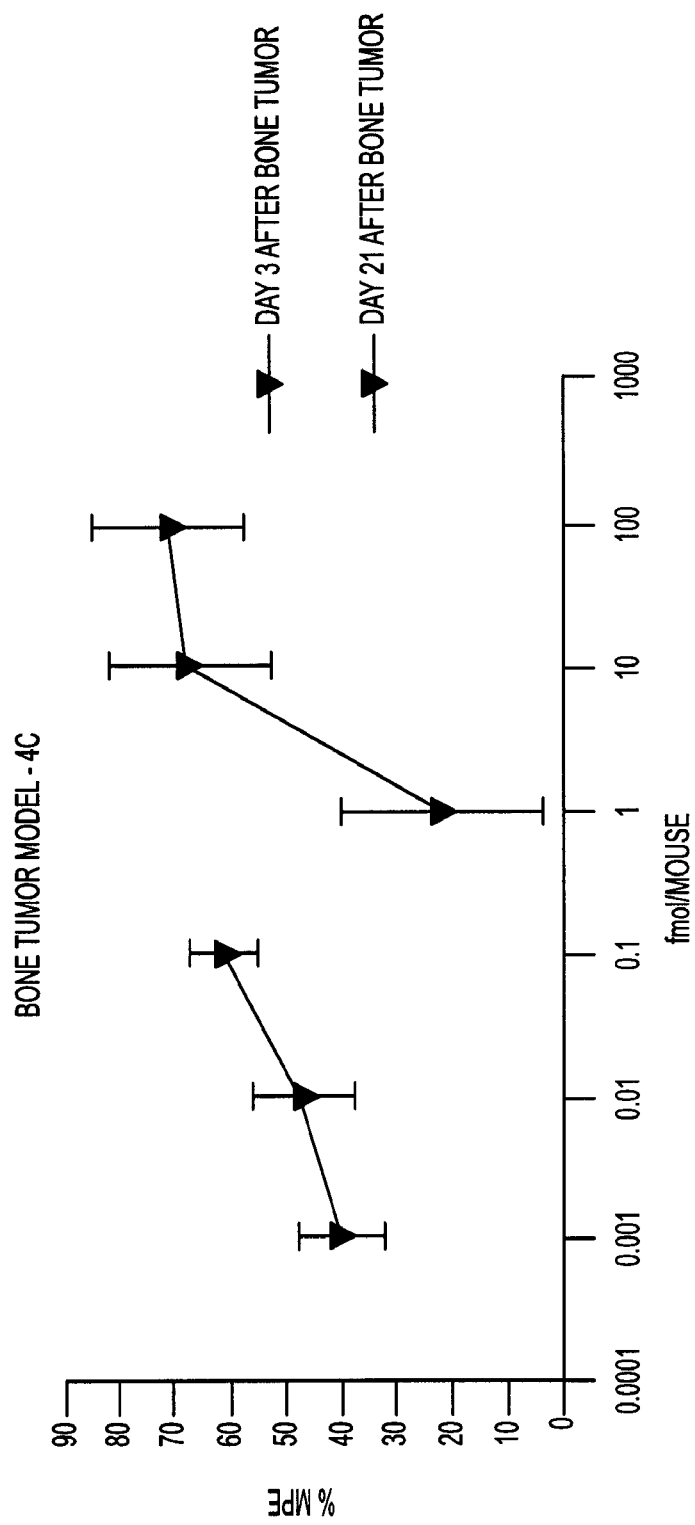
FIG. 2 Illustrates antinociception of i.t. compound 4c increasing in potency from PID 3-21. (Example 5).
Figure 3:
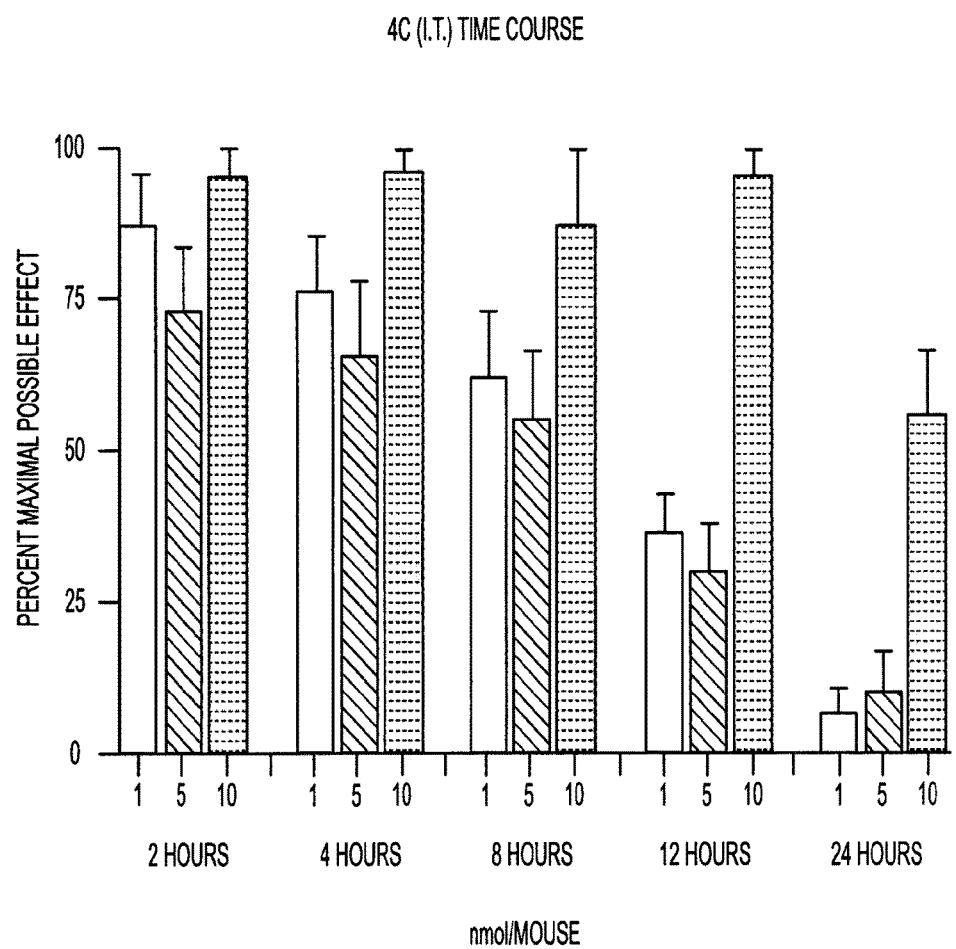
FIG. 3 Illustrates antinociceptive potency of compound 4c in mice pretreated with LPS. (Example 5).

It is well known that $mGluR_5$ receptors are abundantly expressed in spinal cord (Dolan S & Nolan A M, *Neuropharmacology*, 2000, 39, 1132-1138) and have been shown to play important roles in modulation of nociceptive transmission. The $mGluR_5$ subtype is expressed both presynaptically and postsynaptically in the spinal dorsal horn. In addition to being present in neurons, $mGluR_5$ is expressed also in astrocytes, particularly in the spinal cord (Silva G A, et al., *Neurosci. Lett.*, 1999, 263(2-3), 117-120). They participate in the initiation and maintenance of persistent pain induced by tissue inflammation, nerve injury, and bone cancer (Nicholson K J, et al., *Neuroscience*, 2012, 209(0), 87-195; and Gwak Y S & Hulsebosch C E, *Exp. Neurol.*, 2005, 195(1), 236-243). Ren et al. induced progressive bone cancer pain in C3H/HeNCrlVr mice and observed that $mGluR_5$ expression was up-regulated. Up-regulation reached maximum on day 21 postinoculation. Intratheical administration of $mGluR_5$ antagonist MPEP attenuated bone cancer-evoked spontaneous pain in addition to mechanical allodynia and thermal hyperalgesia (28). Using sarcoma NCTC 2472 cells, we induced bone cancer pain in C3H mice and initiated antinociceptive studies using bivalent ligands 4c. Bivalent ligand 4c had $ED_{50}=5.72$ fmol/mouse on day 3, and on day 21 the $ED_{50}$ decreased to 0.01 fmol/mouse (FIG. 2). In a parallel study, monovalent agonists 5 and 6 were utilized. Upon i.t. administration 5 the $ED_{80}$ on day 3 was 250,000 fmol and on day 21 it was 50 fmol. Whereas 250 pmol/mouse of 6, a response of 17.59±18.24 and 72.92±18 26% MPE on day 3 and day 21, respectively, was observed. FIG. 3 shows the time-course of antinociception produced by different doses of compound 4c in LPS-pretreated mice from Example 2

Discussion

In LPS pretreated mice (Table 1) bivalent ligands 3, 4a, 4b, 4d produced antinociception in the nmol range when administered i.t., compound 4c (22-atom spacer) had exceptional antinociceptive potency ($ED_{50}$ 8.83 fmol/mouse). Apparently, the 22-atom spacer length is well-suited to optimally bridge MOP and $mGluR_5$ heteromer, in view of the finding that compound 4d with a 24-atom spacer had a 25-fold lower potency ($ED_{50}=250$ fmol/mouse). The finding that compound 4c has about 37,000× greater potency than a mixture of monovalent ligands 5 and 6 antinociception further supports the importance of the spacer for linking the pharmacophores (Table 2).

Significantly, the development of 24-hour tolerance did not occur in LPS-treated mice that were administered bivalent ligands with 20-, 22-, and 24-atom spacers. However, the bivalent ligands with shorter spacers (3, 4a) and the monovalent ligands (5, 5+6) all exhibited tolerance 24-hour after i.t. administration. These data suggest that the modulating action of the MPEP pharmacophore upon the opioid pharmacophore in the bivalent ligands occurs when the bridging of protomers in the MOP-$mGluR_5$ heteromer occurs by virtue of a spacer of suitable length.

The most potent representative compound evaluated, compound 4c, was evaluated further for the inhibition of nociception using the von Frey assay in C3H mice treated with Complete Freund's Adjuvant (CFA). After i.t. administration of compound 4c, its potency ($ED_{50}$ about 8 fmol/mouse) was comparable to that obtained with LPS-treated mice (FIG. 1) using the tail-flick assay. The von Frey procedure subsequently was employed in testing compound 4c using C3H mice with bone cancer and found to have comparable potency (about 6 fmol/mouse) on day 3, which appeared to increase to 0.01 fmol/mouse on day 21. One possible explanation for these results could be that the levels of MOPR/$mGluR_5$ may have increased during that period.

Conclusions

In view of the structure-activity relationship of representative bivalent ligands, together with literature reports of pharmacologic interaction between morphine and MPEP in vivo and the existence of MOPR-$mGluR_5$ heteromer in cultured cells, it appears likely that compounds 4b, 4c, and 4d have spacers of sufficient length to accommodate the bridging of their opioid and MPEP pharmacophores to the respective protomer recognition sites on the heteromer. Given the unprecedented i.t. antinociceptive potency of compound 4c (fmol range) and its absence of tolerance in the tail-flick and von Frey assays under inflammatory conditions, this ligand has potential for development as a spinally administered analgesic for intractable pain conditions that may be refractory to morphine or other analgesics. In this regard, the ability of compound 4c to effectively treat chronic pain associated with bone cancer is a possibility, particularly in view of its high potency and lack of tolerance. Compound 4c, as well as other compounds of the invention, may also be useful as pharmacological tools to investigate MOPR-$mGluR_5$ in vivo and in vitro.

Examples 3 and 4 illustrate additional conjugates of the invention as well as synthetic intermediates that can be used to prepare such conjugates. All novel compounds illustrated in Examples 3 and 4 are compounds of the present invention.

Example 3: Additional Conjugates of the Invention
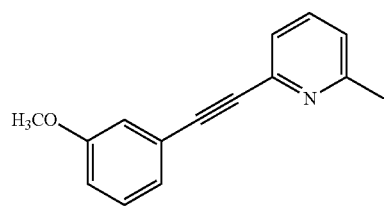
31
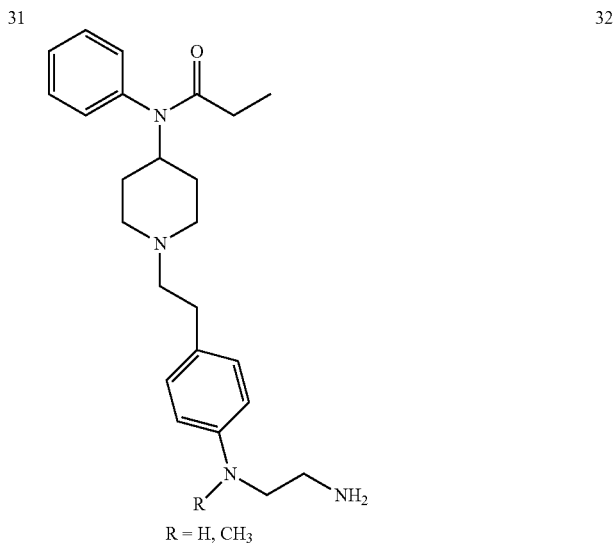
32
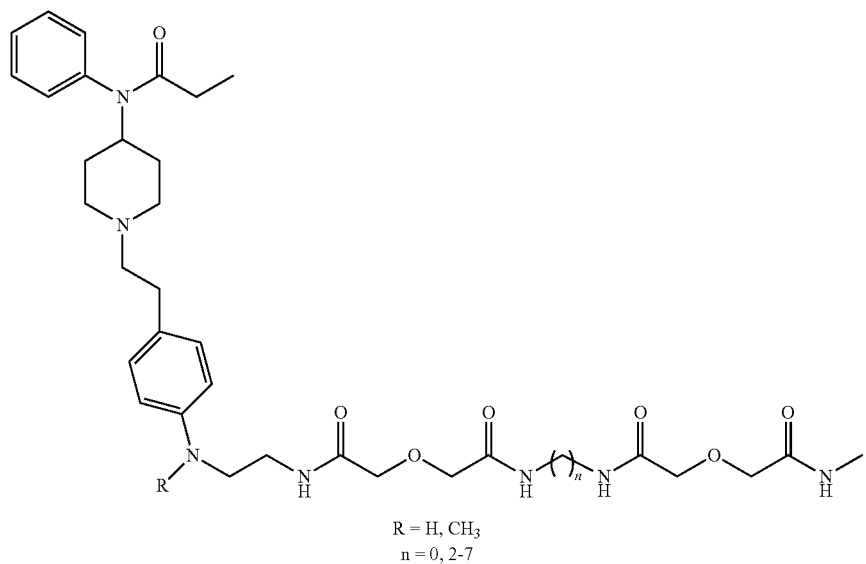
33
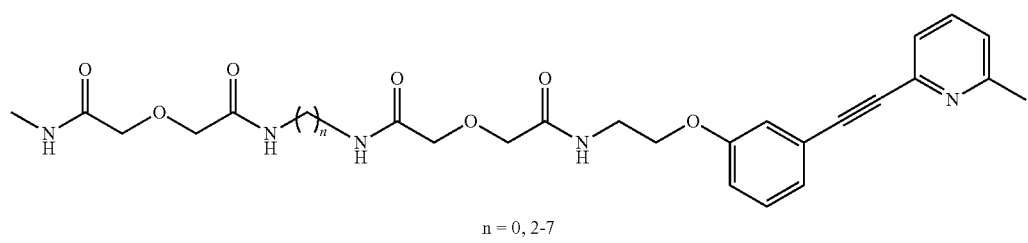
34

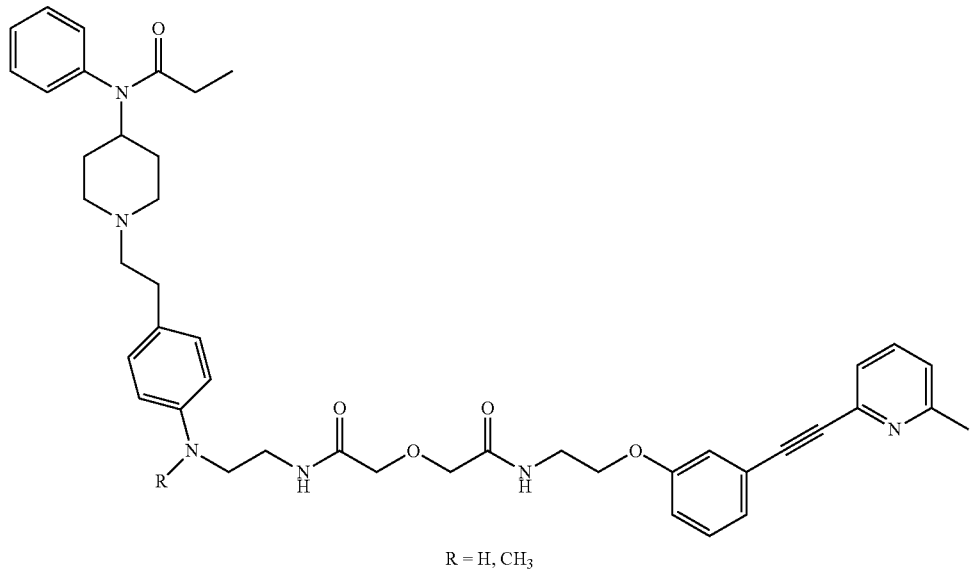
R = H, CH₃
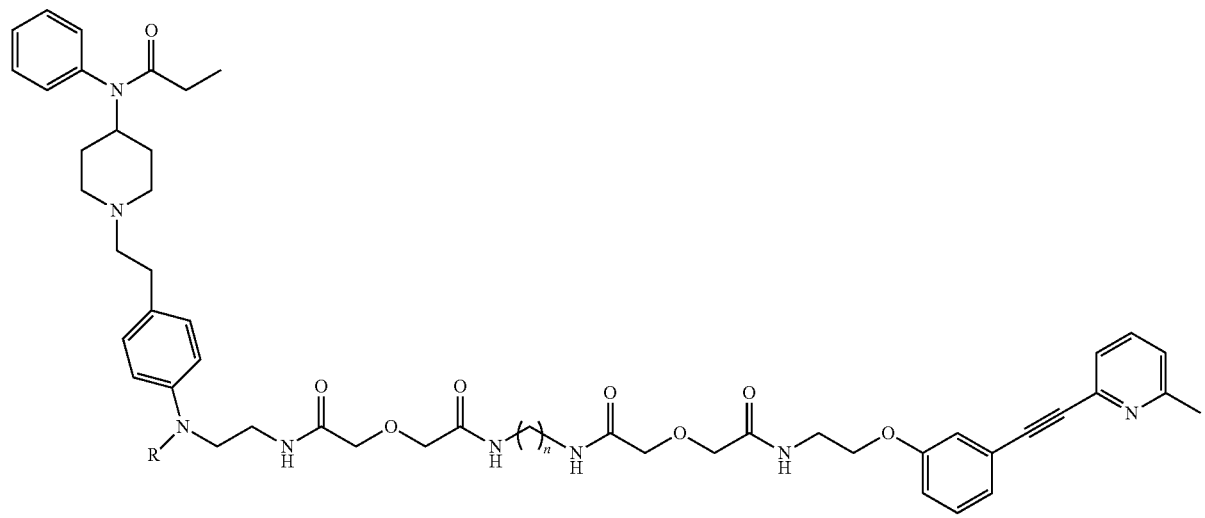
n = 0, 2-7, R = H, CH₃

Example 4: Additional Conjugates of the Invention
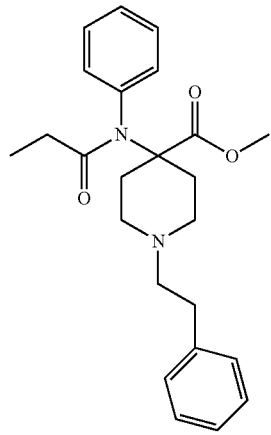
41
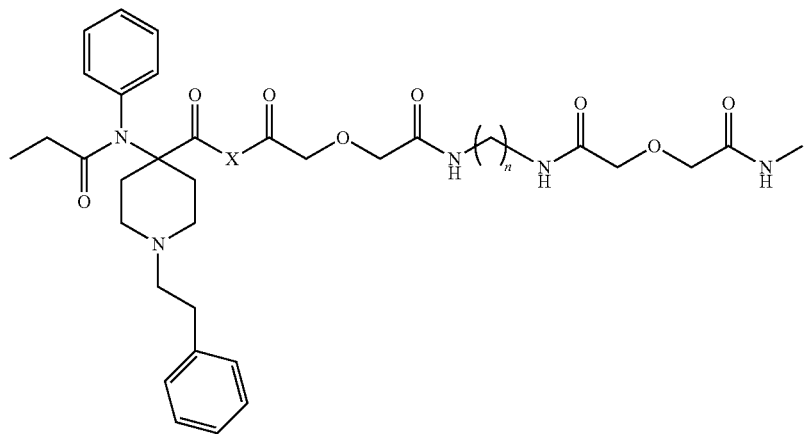
n = 0, 2-7
X = HN(CH₂)₂NH,
O(CH₂)₂NH
42
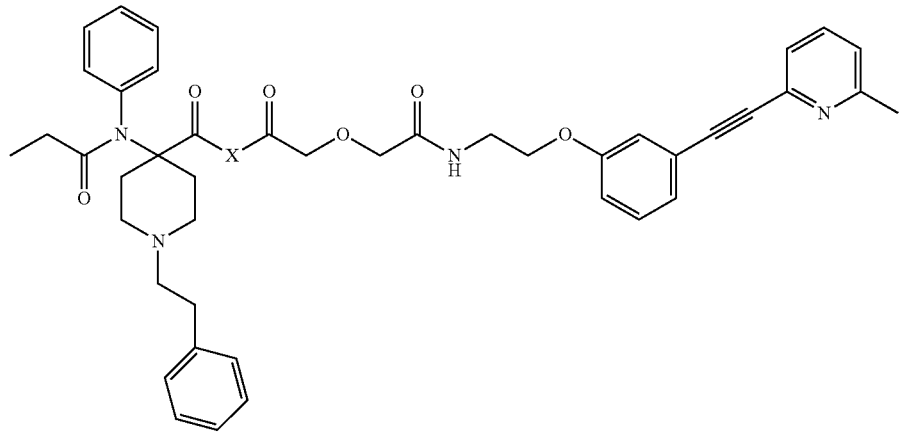
n = 0, 2-7
X = HN(CH₂)₂NH,
O(CH₂)₂NH
43

-continued

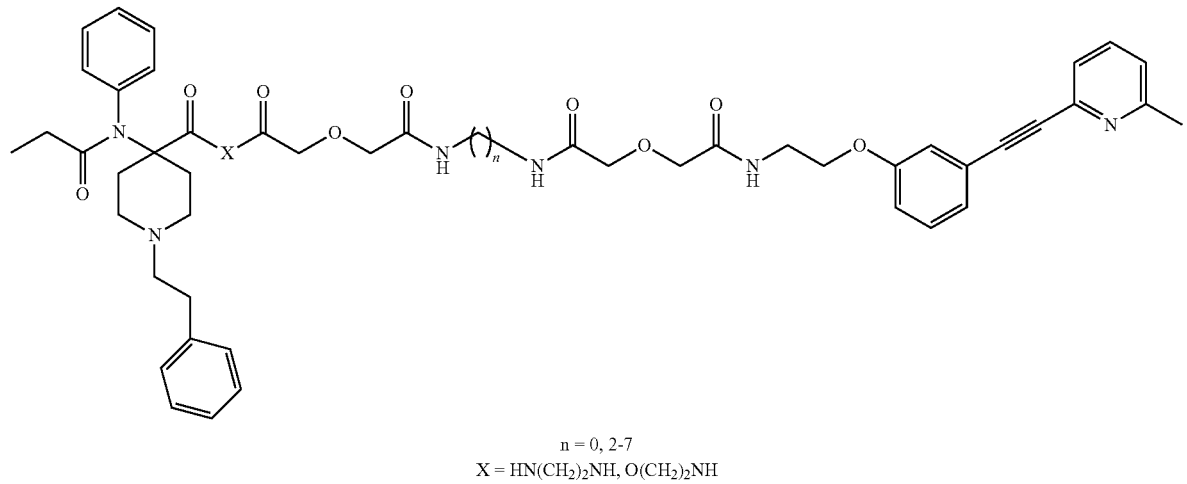

n = 0, 2-7
X = HN(CH$_2$)$_2$NH, O(CH$_2$)$_2$NH

Example 5: Respiratory Depression

Respiratory depression was measured in live mice using the Mouse Ox (small animal Oximeter from STARR Life Sciences Corp, Oakmont, Pa.). CollarClip™ (Un-Anesthetized Neck Sensor) for mice was used as the site for measuring the data.

Day one of each experiment involved training the animals using a disposable CollarClip™. The collar was left on for approximately one hour.

Respiratory depression was considered positive if the O$_2$ saturation decreased from 96-99% to less than 90%. Mice were monitored for a 60-minute period, with measurements 10-20-30 and 60 minutes.

| Compound | Dose is # times the ED$_{90}$ | % of mice with O$_2$ Saturation less than 90% |
|---|---|---|
| Morphine (i.t.) | 100 | 50 |
| 4c (i.t. - LPS) | 50,000 | 0 |
| 4c (i.t. - LPS) | 100,000 | 100 |

The above data demonstrates that compound 4c has a greater safety margin than morphine.

Example 6: Rodent Model of Chronic Bone Cancer Pain

The effectiveness of compound 4c in reducing chronic pain arising from tumor-induced hyperalgesia was evaluated using an established rodent model of chronic bone cancer pain. Significantly, in contrast to morphine, which is known to induce tolerance, intrathecal (i.t.) administration of compound 4c produces profound antinociception without tolerance that becomes more potent during cancer progression in tumor bearing mice.

Methods

Cell Culture.

National Collection of Type Cultures (NCTC) clone 2472 fibrosarcoma cells, originally derived from a connective tissue tumor in a C3H mouse, were obtained from the American Type Cell Culture Collection (Rockville, Md.). Cells were grown and maintained in accordance with standard cell culturing techniques. NCTC cells were grown to 80-90% confluence in 75 cm$^2$ flasks (Corning, Lowell, Mass.) in Dulbecco's Modification of Eagles Medium (Invitrogen, Carlsbad, Calif.) fortified with 10% Horse Serum and sodium bicarbonate. Cell cultures were housed in a water-jacketed incubator with 5% carbon dioxide at 37° C.

Animals.

A well-established rodent hind paw model of bone cancer pain (Wacnik P W, et al., *J Neurosci*. 2001, 21(23), 9355-66) was to examine the effects of representative bivalent ligands on tumor-induced nociception. The inbred C3H/He line is syngeneic to the fibrosarcoma cells used in these experiments and allows these cells to grow tumors without rejection. Male C3H mice were used for all experiments. Animals were maintained on a 12 hour light/dark cycle with food and water ad libitum.

Implantation.

Cells were prepared for implantation by first pouring off the culture medium and washing with phosphate-buffered saline (PBS). Trypsin was added to flask and placed in incubator for 3 min. Upon detachment, cells were suspended in an ample amount of culture medium to terminate enzymatic activity and centrifuged for 10 min at 1000 g. Fibrosarcoma cells were re-suspended in a known amount of PBS for counting, quantified on a hemacytometer, pelleted and re-suspended in PBS. Fibrosarcoma cells were again re-suspended to a final concentration of 2×10$^5$ cells in 20 µl. Initially, animals were anesthetized in a plexi-glass chamber using 3% isoflurane in 3 L/min oxygen. Once each mouse was completely anesthetized, a maintenance rate of 2% isoflurane in 1.5 L/min oxygen was maintained during the short implantation procedure. Tumor cells were manually injected by boring into the calcaneus bone using a 29½ gauge needle connected to a sterile 0.3 ml insulin syringe. Following injection, mice were allowed to recover in cages on a heating pad. Animals showing any signs of dysfunction (e.g. problems with ambulation, lethargy or excessive bleeding) or any animals in which the tumor did not grow were euthanized and removed from the study. This occurred in less than 1% of the animals used in this study.

Intrathecal Injection.

Compound 3 was synthesized as described by Akgün E, et al., *Proceedings of the National Academy of Sciences*, 2013, 110(28), 1595-9. For in vivo studies, all compounds were dissolved in 10% DMSO and then diluted to less than 1% DMSO in the test solutions. Compounds did not show any anti-nociception when they were diluted to 1% or less DMSO solution. Compounds were administered in a 5-μl volume in conscious mice, intrathecally (i.t.) to determine peak time and $ED_{50}$ (Hylden J L, Wilcox G L., *Eur J Pharmacol.*, 1980, 67(2-3), 313-620).

Mechanical Hyperalgesia.

(Smeester B A, et al., Evidence-based complementary and alternative medicine: eCAM. 2012; 2012:671386; and Smeester B A, et al., Evidence-based complementary and alternative medicine: eCAM. 2013; 2013:387169) Animals were placed under clear glass cups on a wire grid and allowed to acclimate for 30 minutes. Mechanical hypersensitivity was tested using a von Frey filament #3.61, which produces a force of 70 mg, was applied to the plantar surface of each hind paw with enough force to cause it to bow slightly. Starting with the right hind paw, the numbers of positive responses out of a total of 10 applications were recorded. Baseline von Frey measurements were obtained prior to tumor-implantation or saline injection into the calcaneus. Subsequent von Frey measurements were taken prior to compound injection as well as 5, 10 and 20 minutes post-injection on days 3, 7, 10, 14, 17 and 21. Animals with saline injection served as controls for tumor cell implantation and tumor-induced nociception. Behavioral assessments were conducted during the light cycle at approximately the same time each day. The investigator performing the von Frey testing was blinded to the animal and compound injected.

Statistics.

Data shown as mean±SEM. Comparisons between groups were performed using two-way ANOVA with post hoc comparisons using Bonferroni's method (Bonferroni C E. Teoria statistica delle classi e calcolo delle probabilit\'{a}. Pubblicazioni del R Istituto Superiore di Scienze Economiche e Commerciali di Firenze. 1936; 8:3-62). The level of significance was set at p≤0.05.

Study Approval.

Procedures were performed in accordance with the guidelines recommended by the International Association for the Study of Pain and all experimental protocols were approved by the Animal Care and Use Committee at the University of Minnesota.

Results

Tumor-Induced Hyperalgesia

Figure 4:
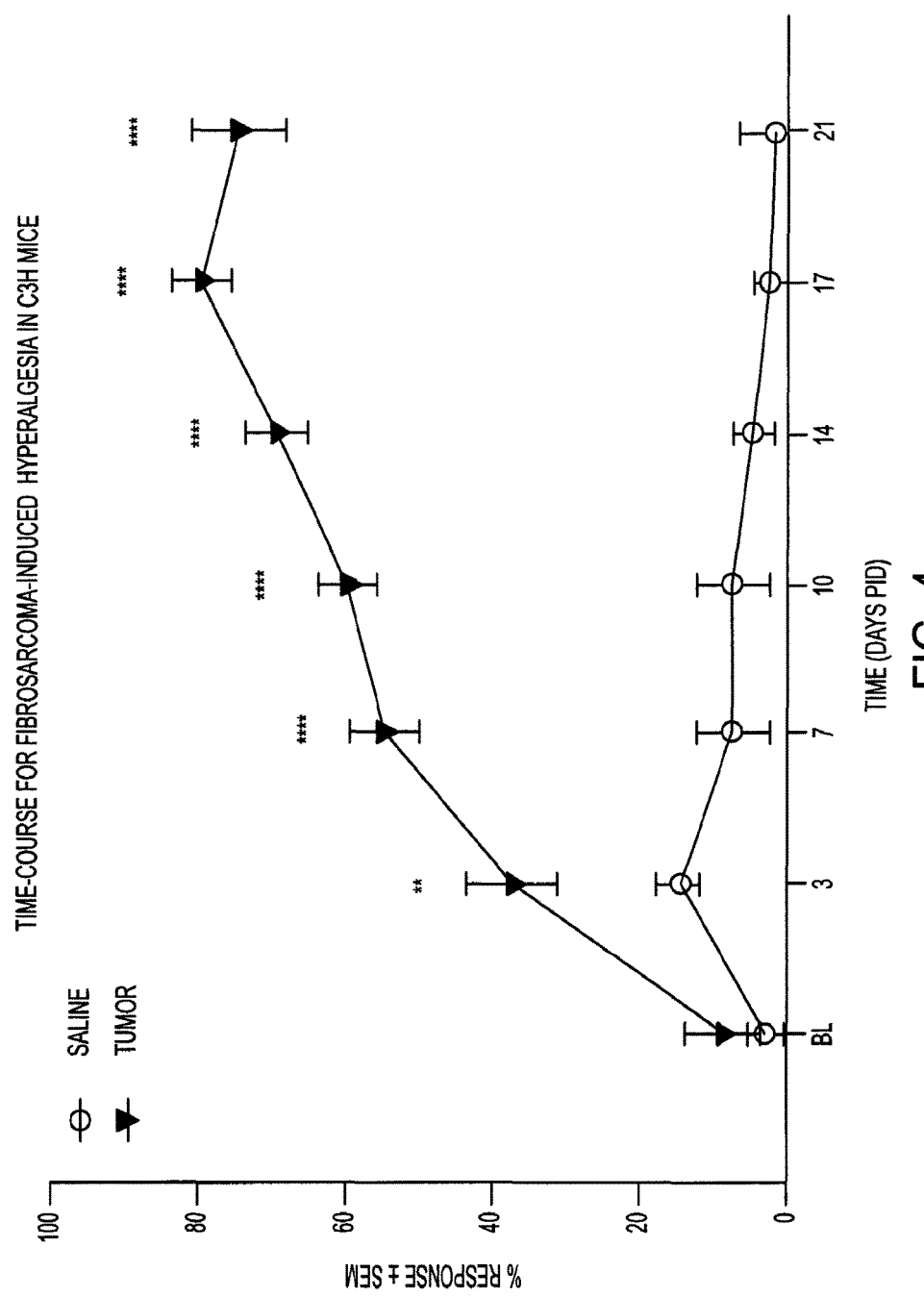
FIG. 4 Shows data from tumor-induced mechanical hyperalgesia from post-implantation day (PID) 3 to 21 in male mice as measured using a von Frey filament applied 10 times to the hind paw (Example 6). Pronounced hyperalgesia is evident as early as PID 3 and extends through PID 21 in males as compared to saline controls (n=4/group, P<0.01 and **P<0.0001).

Implantation of fibrosarcoma cells into the hind paws of C3H mice induced hyperalgesia to normally non-noxious mechanical stimuli as measured using a von Frey monofilament (3.61) when compared to their saline injected controls (FIG. 4, P<0.01, **P<0.0001). This tumor-induced mechanical hyperalgesia, as defined by a significant increase in the number of responses to the von Frey monofilament application, was evident as early as post implantation day (PID) 3 and continued throughout the duration of the experiment.

Bivalency, but not Monovalency Provides Potent Antinociception

Figure 5:
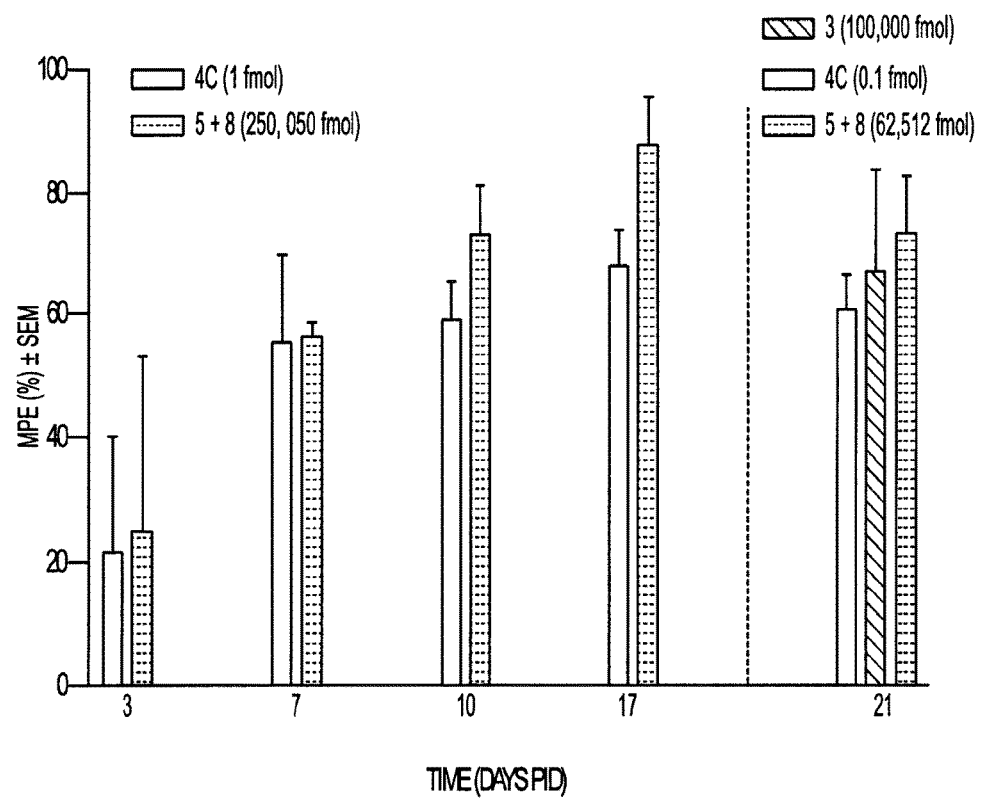
FIG. 5 Illustrates a comparison of equivalent antinociception by bivalents (3,4c) and monovalent (5+6) ligands. Beginning on PID 3 and continuing through the course of the experiment, intrathecal (i.t.) administration of either bivalent ligand 4c or a mixture of monovalent ligands 5 (mu agonist)+6 (mGluR$_5$ antagonist) produced antinociception in tumor-bearing animals. Compound 4c was exceptionally more potent than the combination of monovalent ligands 5 and 6 at all time points evaluated. To investigate the effect of bivalent ligand linker length on potency, compound 3 with a shorter 10-atom linker was evaluated at PID 21 and compared to compound 4c or its co-administered monomers (5+6). 3 was more potent than the mixture, but less potent than compound 4c (n=4-11/group).

The compounds of interest were administered i.t. in fibrosarcoma-bearing mice on PID 3, 7, 10, 14 and 17 and were behaviorally tested using a von Frey monofilament (3.61). Beginning on PID 3, administration of either bivalent ligand 4c or a mixture of monovalent ligands M19 (mu agonist)+MG20 (mGluR$_5$ antagonist) produced potent antinociception in tumor-bearing mice. Compound 4c was exceptionally more potent (about 250,000-fold) than a mixture of monovalent ligands at all time points evaluated (FIG. 5). To investigate the effect of bivalent ligand linker length on potency, a member of the this series with a 10-atom linker (3) was evaluated at PID 21 and compared to 4c or its co-administered monomers (5+6). 3 was about 62,000 more potent than the mixture, but about 100,000-fold less potent than compound 4c (FIG. 5).

The Potency of 4c Increases with Growth of Fibrosarcoma

Figure 6:
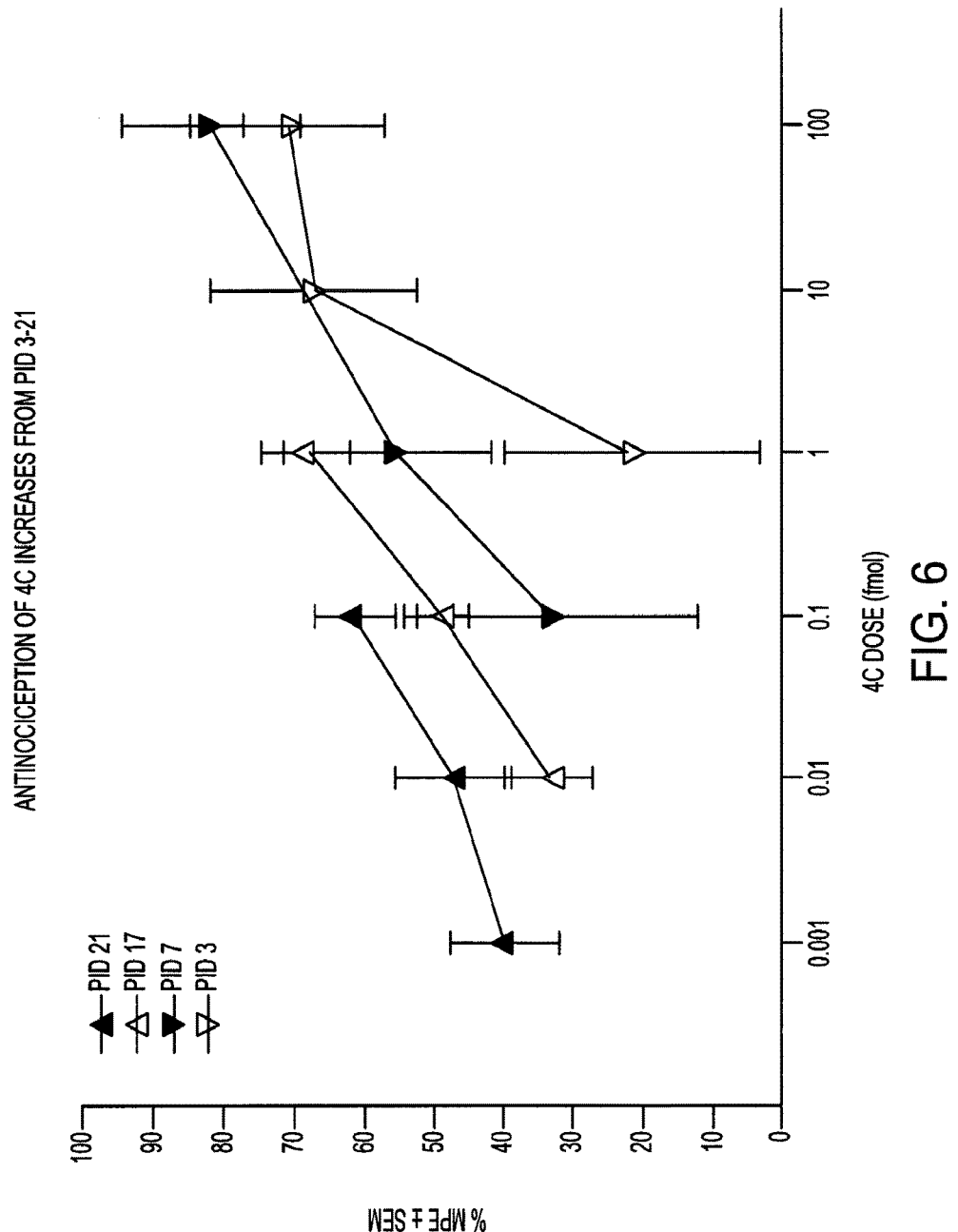
FIG. 6 Illustrates antinociception of i.t. compound 4c increases from PID 3-21. The increasing potency occurred at all subsequent time points tested. The shift in dose-response over a 17-day period (PID 3-21) resulted in about a 600-fold increase in potency.

After i.t. administration, compound 4c was evaluated for its anti-hyperalgesia effect in fibrosarcoma-bearing mice. Beginning from PID 3, increased potency was observed at all time points tested (FIG. 6). A shift in the dose-response relationship can be seen over time, resulting in a about 600-fold greater potency from PID 3-21 (FIGS. 2 and 6).

Single Administration of 4c Promotes Long Duration Antinociception

Figure 7:
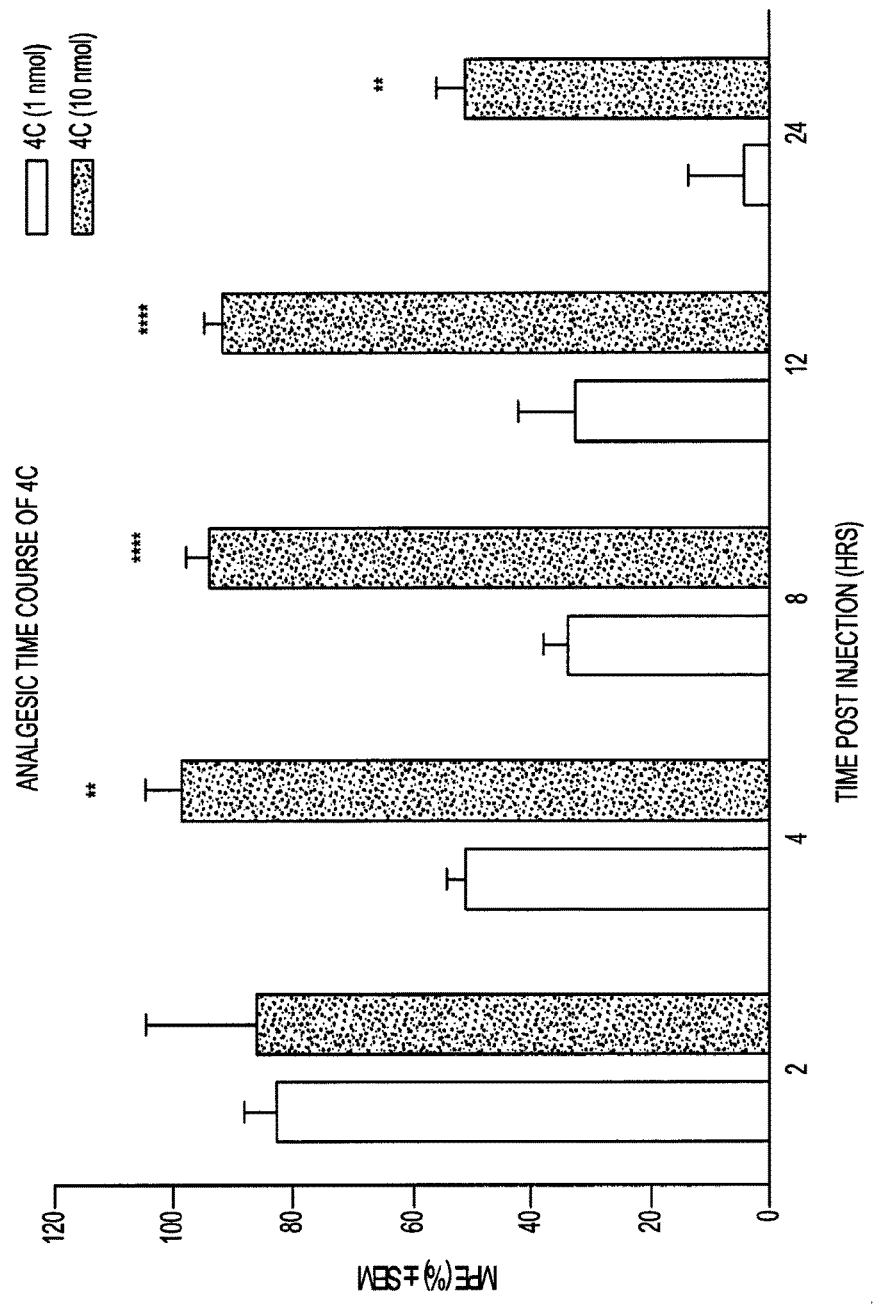
FIG. 7 Illustrates the time-course of antinociception produced after i.t. administration of compound 4c (1 or 10 nmol) in tumor-bearing animals on PID 21 where the hyperalgesic threshold is lowest (see FIG. 4). Potent antinociception is maintained over 24 hours in animals receiving a 10 nmol dose and compared with animals receiving 1 nmol (n=5/group; P<0.01 and **P<0.0001).

Compound 4c was evaluated for effectiveness over a period of 24 hours using 1 and 10 nmol doses in tumor-bearing mice after PID 21 when the hyperalgesic threshold has plateaued (See FIG. 4). The results of this study (FIG. 7) revealed that potent antinociception was maintained over the next 24 hours in mice receiving a 10 nmol i.t. injection of compound 4c. Mice that received a 1 nmol dose exhibited significant antinociception for 12 hours (FIG. 7, P<0.01, P<0.0001).

Discussion

Compound 4c Possesses unprecedented antinociception in two mouse models of inflammatory pain. In this regard, both the LPS-pretreated mouse tail-flick assay and the von Frey assay afforded $ED_{50}$ values in the fmol range for antinociception. It is noteworthy that the unusually high potency in these animal models occurs only upon spinal delivery of compound 4c which was >40,000× greater than by the intracerebroventricular (i.c.v.) route. Significantly, no tolerance or respiratory depression was noted, and the therapeutic index was estimated to be greater than a million.

As tolerance is a major drawback in the chronic administration of opiates, and in view of the favorable therapeutic profile of compound 4c in treating LPS-induced inflammatory pain in mice, the present study involved evaluating its utility for treatment of allodynia/hyperalgesia associated with chronic cancer pain. Because metastatic bone cancer is one of the most common malignancies in patients with prostate or breast cancer, compound 4c was evaluated in an established mouse model of chronic bone cancer pain given its high potency in a dose range that produces no side effects.

The results of the present study reveal that the bivalency of compound 4c is essential for its high potency in bone cancer mice, as a substantially lower potency was observed for a mixture of monovalent ligands (5+6). This is because the length of the linker that tethers the pharmacophores in the bivalent MMG series is critical for targeting a putative MOR-mGluR$_5$ heteromer. In this regard, the 22-atom linker in compound 4c appears to be optimal for simultaneous interaction with both protomers in the heteromer, while the shorter linker (10-atoms) in compound 3 does not permit this to occur as easily.

Both the metabotropic and ionotropic glutamate receptors (mGluR$_5$ and NMDAR) are localized as signaling partners on postsynaptic terminals of neurons, and they are associated with each other via a Homer-Shank synaptic protein complex (Piers T M, et al., *Front Neuropharmacol.*, 2012, 6, 99; and Niswender C M, et al., *Annu Rev Pharmacol Toxicol.*, 2010, 50, 295-322). The reported association of mGluR$_5$ and MOR with subunits NR2 and NR1 (Rodriguez-Munoz M, et al., *Neuropsychopharmacology*, 2012, 37, 38-49), respectively, of NMDAR suggests that in inflammatory states the MOR-mGluR$_5$ heteromer rather than individual homomers associate with these subunits.

In this regard, the bivalency of compound 4c confers an advantage over a mixture of monovalent ligands in part because of the favorable entropic effect due to tethering of the pharmacophores. From this perspective, compound 4c produces potent blockage of hyperalgesia via interaction with both the mGluR$_5$ and MOR protomers of the MOR-mGluR$_5$ heteromer that becomes associated with the NMDAR in the inflammatory state. This may involve specific alignment with NR1 and NR2 subunits of the NMDAR.

In summary, the prominent features observed for compound 4c after intrathecal delivery are a) the absence of tolerance over a period of 7 to 21 days after inoculation with fibrosarcoma cells and b) the long duration of action (>24 hours) after a single 10 nmol i.t. injection. These properties suggest that compound 4c is a viable option for the efficacious pharmacotherapy of chronic inflammatory pain arising from cancer or other conditions.

Example 7

Figure 8:
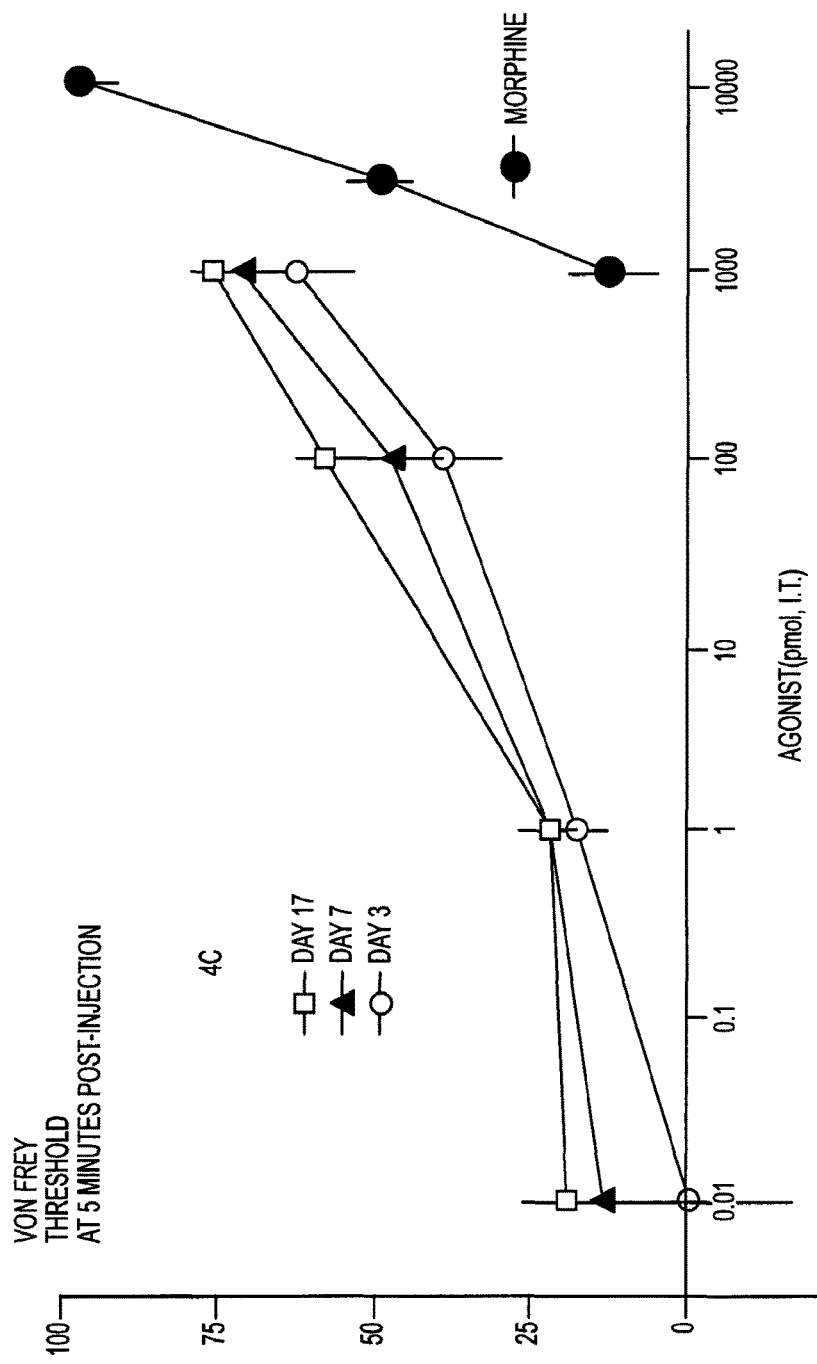
FIG. 8 Illustrates dose-response curves of intrathecal administration of compound 4c (Days 3, 7, 17 post-surgery) and morphine (day 7 post-surgery) in mice with spared nerve Injury (5 minute time point). The data was generated using a procedure similar to that described by Osikowicz M, Mika J. et al., *Pain,* 2008, Vol. 139.
Figure 9:
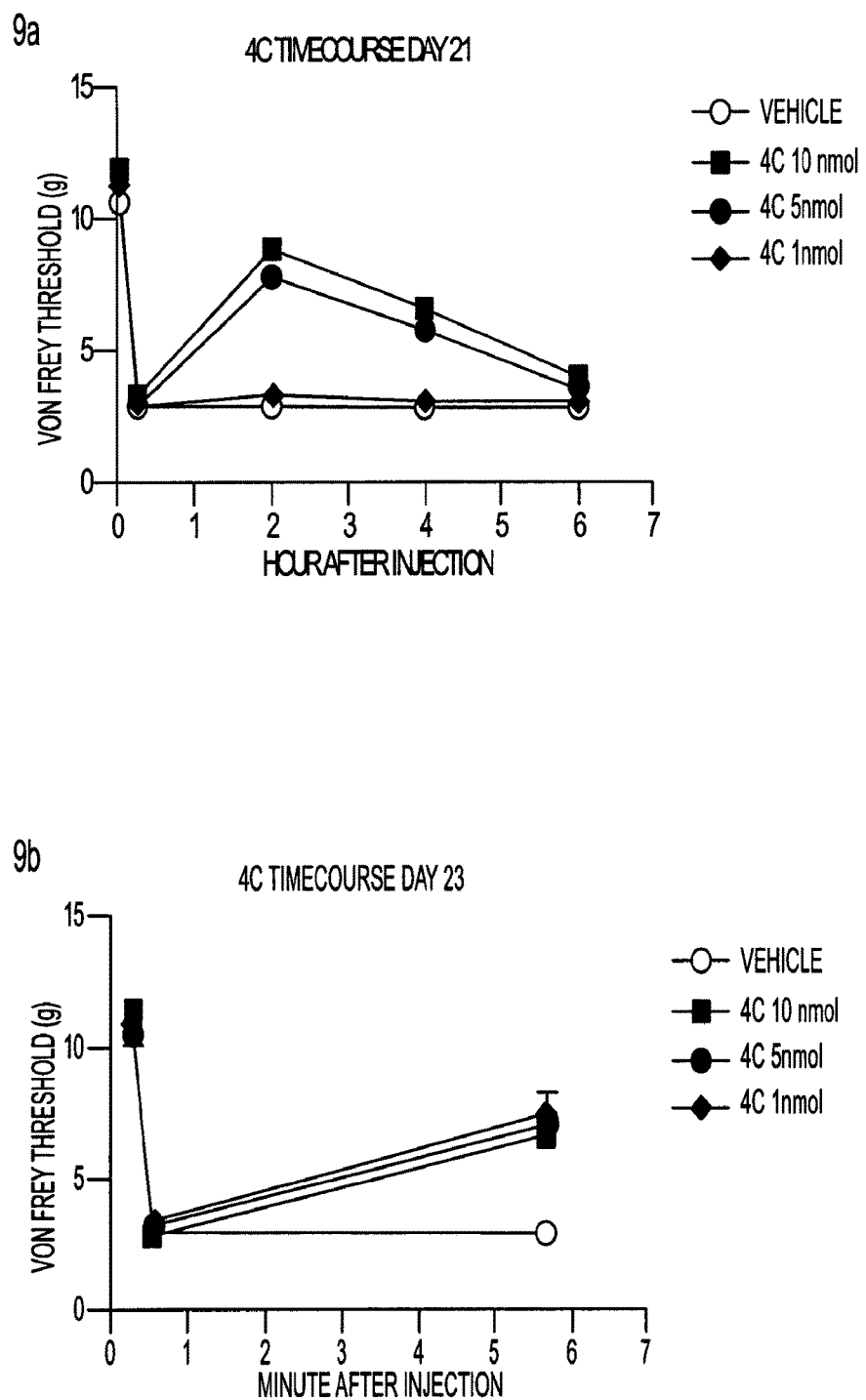
FIG. 9 Illustrates the time course of intrathecal administration of compound 4c, post-injury duration of action: a. 2, 4, and 6 hours post-injection; and b. 5 minutes post-injection (for comparison to lower doses). The data was generated using a procedure similar to that described by Osikowicz M, Mika J. et al., *Pain,* 2008, Vol. 139.

Using a procedure similar to that described by Oskowicz M, Mika J. et al., *Pain,* 2008, 139, 117-136, the data in FIGS. 8-9 was generated for Compound 4c.

Example 8

The following illustrate representative pharmaceutical dosage forms, containing a conjugate of the invention ('Compound X'), for therapeutic or prophylactic use in humans.

| | mg/tablet |
|---|---|
| (i) Tablet 1 | |
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |
| (ii) Tablet 2 | |
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| | mg/ml |
|---|---|
| (iv) Injection 1 (1 mg/ml) | |
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (v) Injection 2 (10 mg/ml) | |
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A conjugate having the formula:

$$R_1-X-R_2$$

wherein:

R$_1$ is a mu opioid receptor agonist having the following formula:

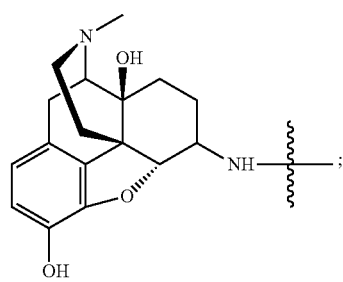

R$_2$ is a mGluR$_5$ antagonist having the following formula:

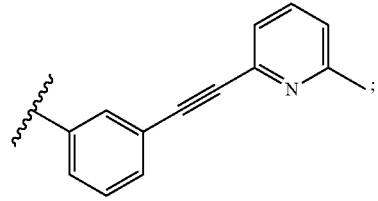 [SMILES: *c1cccc(C#Cc2cccc(C)n2)c1]

X is a linker selected from the group consisting of —CO—CH$_2$OCH$_2$CO—NH—(CH$_2$)$_{n2}$NH—CO—CH$_2$OCH$_2$CO—, —CO—CH$_2$O(CH$_2$CH$_2$O)$_{n3}$CH$_2$CO—, —(CO—CH$_2$NH)$_{x2}$—CO—(CH$_2$)$_{n4}$—CO—(NH—CH$_2$CO)$_{x2}$—, —CO—(CH$_2$)$_{n3}$CO—,

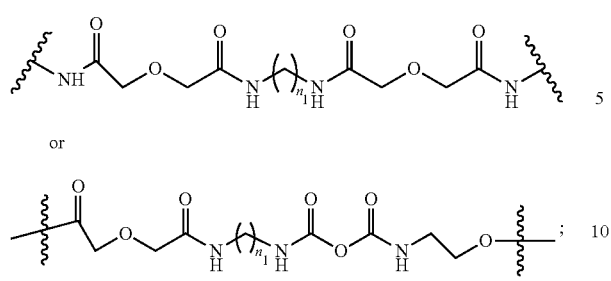

n1 is any integer from 1-10;
n2 is any integer from 1-8;
n3 is any integer from 1-20;
n4 is any integer from 12-22; and
x2 is any integer from 1-2;
or a salt thereof.

2. The conjugate of claim 1 wherein the Mu opioid receptor agonist has the following formula:

3. The conjugate of claim 1 wherein X has the following structure:

wherein $n_1$ is 1, 2, 3, 4, 5, 6, 7, 8, 9, or 10.

4. The conjugate of claim 3 wherein $n_1$ is 3, 4, 5, 6, or 7.

5. The conjugate of claim 3 wherein $n_1$ is 5.

6. A pharmaceutical composition comprising a conjugate as described in claim 1 and a pharmaceutically acceptable carrier.

7. A method for treating pain in an animal comprising administering a conjugate as described in claim 1, or a pharmaceutically acceptable salt thereof, to the animal.

8. A conjugate which has the formula:

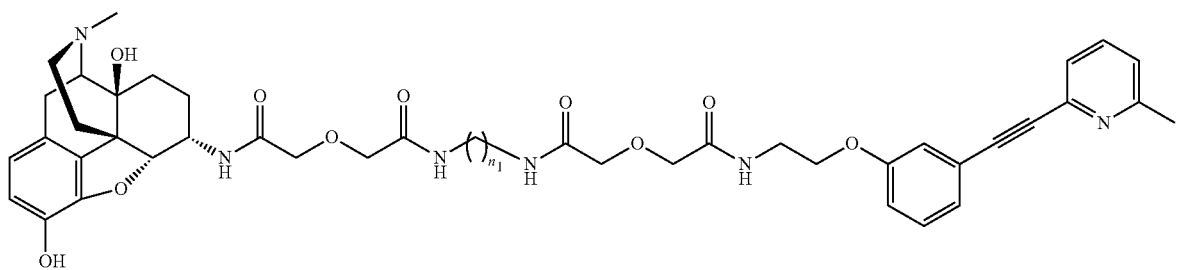

wherein $n_1$ is 2, 3, 5, or 7; or a salt thereof.

9. The compound 4c:
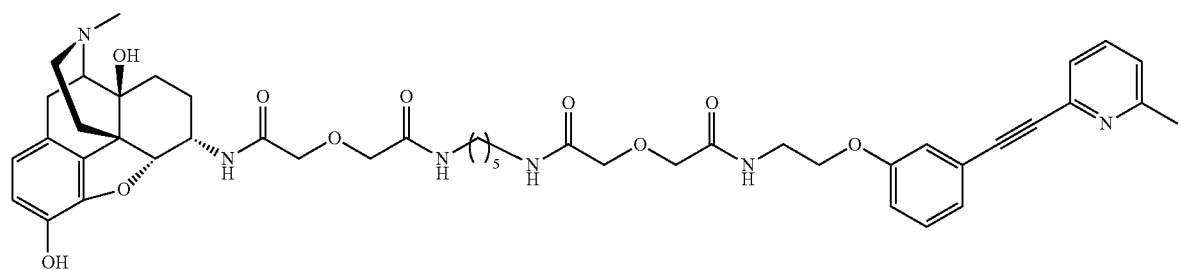
or a salt thereof.

UNITED STATES PATENT AND TRADEMARK OFFICE
CERTIFICATE OF CORRECTION

PATENT NO. : 9,981,043 B2
APPLICATION NO. : 14/766715
DATED : May 29, 2018
INVENTOR(S) : Philip Portoghese and Akgün Eyup It is certified that error appears in the above-identified patent and that said Letters Patent is hereby corrected as shown below:

In the Claims

Column 49, Lines 8-12, Claim 1, the compound should read as follows:

-- 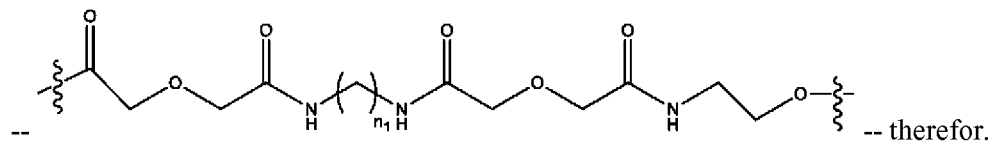 -- therefor.

Signed and Sealed this
Tenth Day of July, 2018

Andrei Iancu
*Director of the United States Patent and Trademark Office*